United States Patent [19]

Slade et al.

[11] Patent Number: 4,477,464

[45] Date of Patent: Oct. 16, 1984

[54] HETERO-BENZAZEPINE DERIVATIVES AND THEIR PHARMACEUTICAL USE

[75] Inventors: Joel Slade, Carmel; James L. Stanton, Ossining, both of N.Y.

[73] Assignee: Ciba-Geigy Corporation, Ardsley, N.Y.

[21] Appl. No.: 465,694

[22] Filed: Feb. 10, 1983

[51] Int. Cl.$^3$ .................... A61K 31/55; C07D 513/04
[52] U.S. Cl. .................... 424/275; 424/244; 424/263; 260/239.3 B; 260/239.3 T
[58] Field of Search ............ 260/239.3 B, 239.3 T; 424/244, 275, 263

[56] References Cited

U.S. PATENT DOCUMENTS

| | | | |
|---|---|---|---|
| 3,661,927 | 5/1972 | Zimkovic | 260/239 BB |
| 3,748,321 | 7/1973 | Krapcho | 260/239 BB |
| 4,410,520 | 10/1983 | Watthey | 424/244 |
| 4,416,819 | 11/1983 | Nagao et al. | 260/239.3 B |

FOREIGN PATENT DOCUMENTS

| | | | |
|---|---|---|---|
| 68173 | 1/1983 | European Pat. Off. | 260/239.3 R |
| 2905637 | 8/1979 | Fed. Rep. of Germany | 260/239.3 B |

OTHER PUBLICATIONS

Levai A., Acta Chimica Academie Scientiariam Hungaricae, vol. 102, pp. 141-142, (1979).
Levai A., Pharmazie, vol. 35, pp. 680-681, (1980).
Ito, S., Bull. Chem. Soc. Jap., vol. 43, p. 1824, (1970), Chem Abstr. vol. 92, item 22531a.
Evans et al., J. Chem. Soc., (1965), pp. 4806-4812.
G. S. Sidhu et al., J. Chem. Soc., (1966), pp. 969-971.

*Primary Examiner*—Robert T. Bond
*Attorney, Agent, or Firm*—Norbert Gruenfeld

[57] ABSTRACT

Disclosed are variously substituted 3-(carboxymethylamino)-(1,5-benzothiazepin-4-one, 1,5-benzoxazepin-4-one and 1,5-benzodiazepin-4-one)-5-alkanoic acids and derivatives as angiotensin-converting enzyme inhibitors and antihypertensive agents. Their synthesis, pharmaceutical compositions thereof, and methods of threatment utilizing such compounds are included.

18 Claims, No Drawings

HETERO-BENZAZEPINE DERIVATIVES AND THEIR PHARMACEUTICAL USE

SUMMARY OF THE INVENTION

The present invention is based upon the discovery that certain substituted 3-amino-(1,5-benzothiazepin-4-one, 1,5-benzoxazepin-4-one and 1,5-benzodiazepin-4-one)-5-alkanoic acids and derivatives represent novel and potent angiotensin-converting enzyme (ACE) inhibitors.

The foregoing attributes render the compounds of this invention particularly useful when administered, alone or in combination, to mammals, e.g. for the treatment or prevention of diseases responsive to inhibition of angiotensin converting enzyme e.g., cardiovascular disorders such as hypertension and cardiac conditions such as congestive heart failure.

DETAILED DISCLOSURE

This invention relates to novel compounds of formula I useful as angiotensin-converting enzyme inhibitors, processes for preparing same, pharmaceutical compositions comprising said compounds, and methods of treating diseases responsive to inhibition of angiotensin-converting enzyme by administration of said compounds and compositions to mammals.

The compounds of the invention are characterized by the general formula I

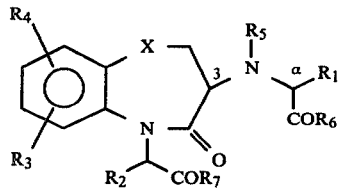

(I)

wherein $COR_6$ and $COR_7$ are independently, carboxy, esterified carboxy, carbamoyl or substituted carbamoyl;

$R_1$ is hydrogen, lower alkyl, amino-lower alkyl, acylamino-lower alkyl, aryl, aryl lower alkyl, cycloalkyl or cycloalkyl lower alkyl;

$R_2$ is hydrogen or lower alkyl;

$R_3$ and $R_4$, each independently, represent hydrogen, lower alkyl, lower alkoxy, lower alkanoyloxy, hydroxy, halogen, trifluoromethyl; or $R_3$ and $R_4$ taken together represent lower alkylenedioxy;

$R_5$ is hydrogen or lower alkyl; and

X represents $S(O)_p$, N—$R_8$ or O, in which radicals $R_8$ represents hydrogen, lower alkyl or aryl, and p represents zero, one or two; and wherein the carbocylic ring may also be hexahydro; and salts thereof, especially pharmaceutically acceptable salts.

More particularly the invention relates to the compounds of formula I wherein $R_1$, $R_2$, $R_3$, $R_4$, $R_5$ and X are as defined above; $R_6$ and $R_7$ represent independently hydroxy; lower alkoxy; (amino, mono- or di-lower alkylamino)-substituted lower alkoxy; carboxy-substituted lower alkoxy, e.g. α-carboxy-substituted lower alkoxy; lower alkoxycarbonyl-substituted lower alkoxy, e.g. α-lower alkoxycarbonyl-substituted lower alkoxy; aryl-substituted lower alkoxy, e.g. optionally substituted benzyloxy or pyridylmethoxy; (hydroxy, lower alkanoyloxy or lower alkoxy)-substituted lower alkoxy, e.g. pivaloyloxymethoxy; (hydroxy, lower alkanoyloxy or lower alkoxy)-substituted lower alkoxymethoxy; bicycloalkoxycarbonyl-substituted lower alkoxy, e.g. bicyclo[2,2,1]heptyloxycarbonyl-substituted lower alkoxy, especially bicyclo[2,2,1]heptyloxycarbonyl-substituted methoxy; 3-phthalidoxy; (lower alkyl, lower alkoxy, halo)-substituted 3-phthalidoxy; amino; lower alkylamino; di-lower alkylamino; di-lower alkylamino in which both alkyl groups are linked by a carbon to carbon bond and together with the amino nitrogen form a 5-, 6- or 7-membered heterocyclic ring, e.g. pyrrolidino, piperidino, or perhydroazepino; (amino or acylamino)-substituted lower alkylamino; alpha-(carboxy or lower alkoxycarbonyl)-substituted lower alkylamino; aryl substituted lower alkylamino in which aryl is preferably phenyl or indolyl and which can be substituted on the alpha-carbon by carboxy or lower alkoxycarbonyl.

Any prodrug derivatives of compounds of this invention e.g. any pharmaceutically acceptable esters and amides of the mono- or di-carboxylic acids of this invention that may be convertible by solvolysis or under physiological conditions to the said carboxylic acids, e.g. esters and amides cited above, represent a particular object of the invention.

Said esters are preferably, e.g., the straight chain or branched lower alkyl esters unsubstituted or suitably substituted such as the pivaloyloxymethyl, bornyloxycarbonylmethyl, benzyl, pyridylmethyl, alpha-carboxyethyl or suitably esterified alpha-carboxyethyl esters.

Said amides are preferably e.g. simple primary and secondary amides and amides derived from the amino acids or derivatives thereof, such as the amides derived from alanine, phenylalanine.

Preferred are the compounds of formula I, wherein the carbocyclic ring may also be hexahydro, and wherein $R_1$ is lower alkyl, amino-lower alkyl, and aryl-lower alkyl; $R_2$ and $R_5$ independently represent hydrogen or lower alkyl;

$R_3$ and $R_4$ represent independently hydrogen, lower alkyl, lower alkoxy, lower alkanoyloxy, hydroxy, halogen, trifluoromethyl; or $R_3$ and $R_4$ taken together represent lower alkylenedioxy; $R_6$ and $R_7$ represent independently hydroxy, amino, mono- or di-lower alkylamino, lower alkoxy, benzyloxy, pyridylmethoxy, pivaloyloxymethoxy, bicyclo[2,2,1]heptyloxy-substituted methoxy, alpha-carboxyethoxy or alpha-lower alkoxycarbonylethoxy;

X represents O, $S(O)_p$ wherein p represents zero, 1 or 2, or N—$R_8$ wherein $R_8$ represents hydrogen or lower alkyl; and pharmaceutically acceptable salts thereof.

One particular embodiment of the invention is represented by the compounds of formula II.

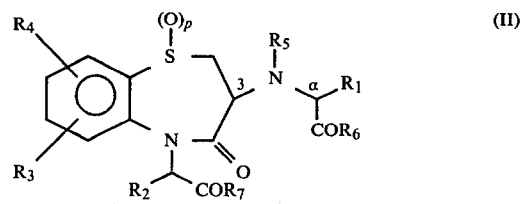

(II)

wherein $R_1$ is hydrogen, lower alkyl, amino-lower alkyl, acylamino-lower alkyl, aryl, aryl-lower alkyl, cycloalkyl-lower alkyl;

$R_2$ and $R_5$ represent hydrogen or lower alkyl;

$R_3$ and $R_4$ represent hydrogen, lower alkyl, lower alkoxy, lower alkanoyloxy, hydroxy, halogen, trifluoromethyl; or $R_3$ and $R_4$ taken together represent lower alkylenedioxy;

p represents zero, one or two;

$R_6$ and $R_7$ independently represent hydroxy, amino, mono- or di-lower alkylamino, lower alkoxy, aryl-lower alkoxy, lower alkanoyloxymethoxy, (amino, mono- or di-lower alkylamino, carboxy, lower alkoxycarbonyl or bicyclo[2,2,1]-heptyloxycarbonyl)-lower alkoxy; or the pharmaceutically acceptable salts thereof.

Preferred are the compounds of formula II wherein $R_1$ is hydrogen, lower alkyl, amino-lower alkyl, acylamino-lower alkyl, aryl-lower alkyl where aryl represents phenyl unsubstituted or mono- or disubstituted by lower alkyl, hydroxy, lower alkoxy, lower alkylenedioxy, lower alkanoyloxy, halogen or trifluoromethyl;

$R_2$ and $R_5$ are hydrogen or lower alkyl;

$R_3$ and $R_4$ are hydrogen, lower alkoxy, lower alkyl, halogen or trifluoromethyl; or $R_3$ and $R_4$ taken together represent alkylenedioxy;

p represents zero, one or two;

$R_6$ and $R_7$ independently represent hydroxy, amino, lower alkoxy, phenyl-lower alkoxy, pyridyl-lower alkoxy, lower alkanoyloxymethoxy, lower alkoxycarbonyl-lower alkoxy, or bicyclo[2,2,1]heptyloxycarbonylmethoxy;

or pharmaceutically acceptable salts thereof.

Particularly preferred are compounds of formula II wherein $R_1$ is hydrogen, lower alkyl, ω-amino-lower alkyl, ω-acylamino-lower alkyl, aryl-lower alkyl where aryl represents phenyl unsubstituted or mono-substituted by lower alkyl, hydroxy, lower alkoxy, lower alkanoyloxy, halogen or trifluoromethyl;

$R_2$ and $R_5$ are hydrogen or lower alkyl;

$R_2$ and $R_5$ are hydrogen or lower alkyl;

$R_3$ is hydrogen;

$R_4$ is hydrogen, lower alkoxy, lower alkyl, halogen, or trifluoromethyl;

p represents zero or one;

$R_6$ and $R_7$ independently represent hydroxy, amino, lower alkoxy, phenyl-lower alkoxy, pyridyl-lower alkoxy, lower alkoxycarbonyl-lower alkoxy; bicyclo[2,2,1]-heptyloxycarbonylmethoxy or lower alkanoyloxymethoxy;

or pharmaceutically acceptable salts thereof.

Especially preferred are compounds of formula II wherein $R_1$ is hydrogen, methyl, ethyl, isopropyl, ω-aminopropyl, ω-benzyloxycarbonylaminobutyl, ω-aminobutyl, aryl-(methyl, ethyl, propyl) where aryl represents phenyl unsubstituted or substituted by one methyl, hydroxy, methoxy, methylenedioxy, acetoxy, chloro or trifluoromethyl group.

$R_2$, $R_3$ and $R_5$ are hydrogen;

$R_4$ represents hydrogen, methoxy, methyl, chloro or trifluoromethyl;

p represents zero or one;

$R_6$ and $R_7$ independently represent hydroxy, amino, ethoxy, methoxy, benzyloxy, ethoxycarbonylmethoxy, pivaloyloxymethoxy, bornyloxycarbonylmethoxy or pyridylmethoxy;

or pharmaceutically acceptable salts thereof.

Especially useful are compounds of formula III

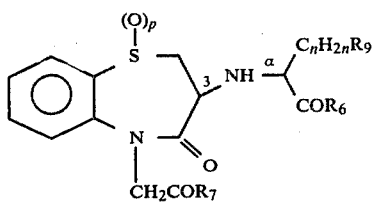

wherein n represents an integer from 1 to 4; p is zero, one or two;

$R_9$ is hydrogen, amino, benzyloxycarbonylamino, phenyl unsubstituted or monosubstituted by lower alkyl, lower alkoxy, lower alkanoyloxy, halogen, hydroxy, or trifluoromethyl;

$R_6$ and $R_7$ independently represent hydroxy, lower alkoxy of up to 4 carbon atoms, benzyloxy, amino;

or pharmaceutically acceptable salts thereof.

Especially valuable are compounds of formula III wherein $C_nH_{2n}$ represents ethylene; $R_9$ represents phenyl or phenyl monosubstituted by lower alkoxy with up to 4 carbon atoms, lower alkyl with up to 4 carbon atoms, halogen or trifluoromethyl; p is zero or one;

$R_6$ and $R_7$ independently represent hydroxy or lower alkoxy with up to 4 carbon atoms;

or pharmaceutically acceptable salts thereof.

Another preferred embodiment of the invention is represented by the compounds of formula IV

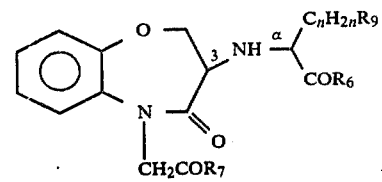

n represents an integer from 1 to 4;

$R_9$ is hydrogen, amino, benzyloxycarbonylamino, phenyl unsubstituted or monosubstituted by lower alkyl, lower alkoxy, lower alkanoyloxy, halogen, hydroxy, or trifluoromethyl;

$R_6$ and $R_7$ independently represent hydroxy or lower alkoxy of up to 4 carbon atoms, or pharmaceutically acceptable salts thereof.

Preferred are said compounds of formula IV wherein n is 2, and $R_9$ is phenyl or substituted phenyl.

According to the present invention one or both of the carboxyl groups of the dicarboxylic acids, i.e. compounds of formulae I to IV wherein $R_6$ and $R_7$ are hydroxy, may be functionalized as esters or amides. These functional derivatives are preferably the mono or bis lower alkyl esters e.g. methyl, ethyl, n- or i-propyl, butyl or benzyl esters. Highly preferred functional derivatives are the mono esters of formulae I to III, e.g. wherein one of $R_6$ and $R_7$ represents hydroxy and the other represents lower alkoxy.

The present invention also relates to the stereoisomers of compounds of formula I. A number of racemates are obtainable when, e.g. in formula I at least one of $R_1$ and $R_2$ is not hydrogen.

The individual enantiomers of said racemates may in turn be obtained. Certain specific said isomers are preferred as angiotensin-converting enzyme inhibitors.

Preferred are said compounds of formula I in which the asymmetric ring carbon (position 3) bearing the substituted amino group is of the (S)-configuration in said compounds where X represents O and NR$_8$ and of the (R)-configuration in said compounds where X represents S(O)$_p$. Further preferred are said compound of formula I in which the said chain asymmetric carbon atom (alpha) bearing the COR$_6$ group is of the (S)-configuration.

Preferred are in turn said compounds of formulae II and III wherein said asymmetric ring carbon atom 3 bearing the substituted amino group is of the R-configuration and the side chain carbon (alpha) bearing the substituted amino group is of the (S)-configuration.

Also preferred are the said compounds of formula IV wherein the chirality is (S) at both ring positions 3 and side chain position alpha.

The general definitions used herein have the following meanings within the scope of the present invention.

Aryl represents a carbocyclic or heterocyclic aromatic radical preferably being phenyl, unsubstituted or mono- or di-substituted by lower alkyl, lower alkoxy, lower alkylenedioxy, lower alkanoyloxy, hydroxy, halogen or trifluoromethyl.

The term cycloalkyl represents a cyclic hydrocarbon radical which preferably contains 3 to 8 carbons and is, for example, cyclopentyl or cyclohexyl.

The term aryl-lower alkyl represents preferably benzyl, 1- or 2-phenylethyl, 1-, 2- or 3-phenylpropyl, 1-, 2-, 3- or 4-phenylbutyl, wherein the phenyl ring is unsubstituted or mono- or disubstituted by lower alkyl, hydroxy, lower alkoxy, lower alkylenedioxy, lower alkanoyloxy, halogen or trifluoromethyl.

The term cycloalkyl-lower alkyl represents preferably 1 or 2-(cyclopentyl or cyclohexyl)-ethyl, 1-, 2- or 3-(cyclopentyl or cyclohexyl)-propyl, or 1-, 2-, 3- or 4-(cyclopentyl or cyclohexyl)-butyl.

The term "lower" referred to above and hereinafter in connection with organic radicals or compounds respectively defines such with up to and including 7, preferably up and including 4 and advantageously one or two carbon atoms.

A lower alkyl group preferably contains 1-4 carbon atoms and represents for example ethyl, propyl, butyl or advantageously methyl.

A lower alkoxy group preferably contains 1-4 carbon atoms and represents for example methoxy, propoxy, isopropoxy or advantageously ethoxy. A mono-lower alkylamino group preferably contains 1-4 carbon atoms in the alkyl portion and is for example N-methylamino, N-propylamino or advantageously N-ethylamino. A di-lower alkylamino group preferably contains 1-4 carbon atoms in each lower alkyl portion and represents, for example, N,N-dimethylamino, N-methyl-N-ethylamino and advantageously N,N-diethylamino.

Lower alkanoyloxy represents preferably acetoxy, propionoxy or pivaloyloxy.

Alkylenedioxy represents preferably ethylenedioxy, and advantageously methylenedioxy.

Aryl-lower alkoxy represents advantageously e.g. benzyloxy, benzyloxy substituted by methyl, methoxy or chloro, and pyridylmethoxy.

Carboxy-lower alkoxy represents advantageously e.g. 1-carboxyethoxy.

Lower alkoxycarbonyl-lower alkoxy represents advantageously e.g. 1-(ethoxycarbonyl)ethoxy.

Amino-lower alkoxy, mono-lower alkylamino-lower alkoxy, di-(lower)alkylamino-lower alkoxy advantageously represent respectively e.g. aminoethoxy, ethylaminoethoxy, diethylaminoethoxy.

Lower alkanoyloxymethoxy represents advantageously e.g. pivaloyloxymethoxy.

Bicycloalkyloxycarbonyl-(lower)alkoxy preferably represents bicyclo[2,2,1]heptyloxycarbonyl-(lower)alkoxy unsubstituted or substituted by lower alkyl, advantageously bornyloxycarbonylmethoxy.

Amino-lower alkyl and ω-amino-lower alkyl represent preferably amino(ethyl,propyl or butyl) and ω-amino(ethyl, propyl or butyl) respectively.

Acylamino-lower alkyl and ω-acylamino-lower alkyl represent preferably acylamino(ethyl, propyl or butyl) and ω-acylamino(ethyl, propyl or butyl) respectively.

Acylamino represents lower alkanoylamino, lower alkoxycarbonylamino, cycloalkylcarbonylamino, cycloalkyloxycarbonylamino, cycloalkyl-lower alkoxycarbonylamino; also aryl-lower alkanoylamino, aryl-lower alkoxycarbonylamino, arylsulfonamido in which aryl preferably represents phenyl or phenyl substituted by preferably lower alkyl, lower alkoxy or halogen; also aroylamino in which aroyl preferably represents benzoyl, or benzoyl substituted by preferably lower alkyl, lower alkoxy or halogen, or nicotinoyl.

Aryl-lower alkoxycarbonylamino represents preferably aryl methoxycarbonylamino, advantageously benzyloxycarbonylamino, (also called carbobenzyloxyamino), benzyloxycarbonylamino substituted on the phenyl ring by lower alkyl, lower alkoxy or halogen, e.g. methyl, methoxy or chloro respectively, or pyridylmethoxycarbonylamino.

Halogen preferably represents chlorine, but may also be bromine, fluorine or iodine.

S(O)$_p$ represents thio (p=0), sulfinyl (p=1) and sulfonyl (p=2) bridge.

O represents the oxygen bridge.

N—R$_8$ represents the R$_8$-substituted amino bridge.

Pharmaceutically acceptable salts are preferably metal or ammonium salts of said compounds of formula I wherein COR$_6$ and/or COR$_7$ represent carboxy, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)amines, lower alkylenediamines or lower hydroxyalkyl or aralkyl)alkylammonium bases, e.g., methylamine, diethylamine, triethylamine, dicyclohexylamine, triethanolamine, ethylenediamine, tris-(hydroxymethyl)aminomethane or benzyltrimethylammonium hydroxide. Said compounds of Formula I form acid addition salts, which are preferably such of therapeutically acceptable inorganic or organic acids, such as strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid.

The compounds of formula I exhibit valuable pharmacological properties, e.g. cardiovascular effects, by inter alia inhibiting the release of Angiotensin II through selective inhibition of angiotensin-converting enzyme in mammals. The compounds are thus useful for treating diseases responsive to angiotensin-converting enzyme inhibition in mammals including man.

The compounds of this invention exhibit primarily hypotensive/antihypertensive and cardiac effects inter alia due to their angiotensin-converting enzyme inhibitory activity. These properties are demonstrable by in vivo or in vitro tests, using advantageously mammals, e.g., rats, cats, dogs or isolated organs thereof, as test objects. The animals may either be normotensive or hypertensive e.g., genetically spontaneous hypertensive rats, or renal hypertensive rats and dogs, and sodium-depleted dogs. The compounds can be applied to the test animals enterally or parenterally, advantageously orally or intravenously, for example within gelatin capsules or in the form of starchy suspensions or aqueous solutions. The applied dosage may range between about 0.01 and 100 mg/kg/day, preferably between about 0.05 and 50 mg/kg/day, advantageously between about 0.1 and 25 mg/kg/day.

The in vivo lowering effect on the blood pressure is recorded, either directly by means of a catheter, placed in the test animal's femoral artery, or indirectly by sphygmomanometry at the rat's tail or a transducer. The blood pressure is recorded in mm Hg prior to and after dosing.

Thus the antihypertensive effects are demonstrable in spontaneously hypertensive rats by indirect measurement of systolic pressure. Conscious rats are placed individually in restraint cages within a gently warmed chamber. A rubber pulse sensor is placed distal to an inflatable occlusive cuff on each rat's tail. The cuff is periodically inflated to occlude the tail artery, and systolic pressure is recorded as the point where the first discernible pulse emerges along the decaying calibrated pressure curve. After obtaining control values of blood pressure and heart rate, test compounds are administered orally once daily for 4 consecutive days. Additional blood pressure measurements are usually made at 2.0, 4.0 and 23.5 hours after each daily dosing, and responses are compared to those of rats dosed with the treatment vehicle.

Illustrative of the invention, the compound of example 3a at a dose of 10 mg/kg p.o. lowers blood pressure by about 35 mm Hg.

The compounds of this invention when administered intravenously or orally also exhibit an inbibitory effect against the Angiotensin I induced pressor response of normotensive rats. Angiotensin I is hydrolyzed by the action of said converting enzyme to the potent pressor substance Angiotensin II. The inhibition of said enzyme prevents the generation of Angiotensin II from I and, therefore, attenuates any pressor response following an Angiotensin I challenge.

The corresponding in vivo test is performed with male, normotensive rats, which are anesthetized with sodium 5-ethyl-5-(1-methylpropyl)-2-thiobarbiturate. A femoral artery and saphenous vein are cannulated respectively for direct blood pressure measurement and the i.v. administration of Angiotensin I and a compound of this invention. After the basal blood pressure is stabilized, pressor responses to 3 challenges of 333 ng/kg angiotensin I i.v., at 5 minute intervals, are obtained. Such pressure responses are usually again obtained at time intervals after i.v. or p.o. administration of the compound to be tested, and compared with the initial responses. Any observed decrease of said pressor response is an indication of Angiotensin I converting enzyme inhibition. Illustrative of this invention, the compound of example 3a inhibits the pressor response following angiotensin I challenge by about 70% at a dose of 10 mg/kg p.o. as measured 2 to 4 hours after administration.

The in vitro inhibition of the angiotensin-converting enzyme by the compounds of this invention can be demonstrated by a method analogous to that given in Biochim. Biophys. Acta 293, 451 (1973). According to this method, said compounds are dissolved at about 1 mM concentration in phosphate buffer. To 100 microliters of solutions of the test compound in phosphate buffer, diluted to the desired concentration, are added 100 microliters of 5 mM hippuryl-histidyl-leucine in phosphate buffer, followed by 50 microliters of the angiotensin-converting enzyme preparation (from lungs of adult male rabbits) in Tris buffer, containing potassium and magnesium chloride, as well as sucrose. Said solutions are incubated at 37° C. for 30 minutes and combined with 0.75 ml of 0.6N aqueous sodium hydroxide to stop further reaction. Then 100 microliters of a 0.2% solution of o-phthalaldehyde in methanol are added at room temperature, and 10 minutes later 100 microliters of 6N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the $IC_{50}$, i.e., the drug concentration which gives half the activity of the control sample containing no drug.

Illustrative of the invention, the compounds of examples 2, 6, 12 and 14 show an $IC_{50}$ of about 10, 3, 6 and 28 nM $(10^{-9}M)$ respectively.

Angiotensin-converting enzyme not only participates in the conversion of Angiotensin I to Angiotensin II, but also plays a role in the control of bradykinin and aldosterone levels. The effect of the compounds of this invention on these factors may also contribute to the antihypertensive and cardiac effects of the compounds of this invention.

The aforementioned advantageous properties render the compounds of this invention of great value as specific therapeutic agents for mammals including man.

Accordingly, the compounds of this invention are valuable antihypertensive agents, especially useful for ameliorating hypertension (regardless of etiology) and/or cardiac conditions, such as congestive heart failure. They are also useful in the preparation of other valuable products, especially of corresponding pharmaceutical compositions.

The compounds of formula I according to the invention can be prepared in a manner which is known per se, e.g. by (a) alkylating a compound of the formula

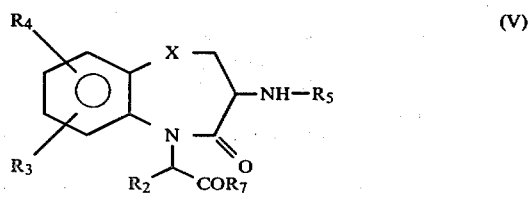

(V)

in which the carbocyclic ring may also be hexahydro, and wherein X, $R_2$ to $R_5$ and $R_7$ have the meanings given hereinabove, with a compound of the formula

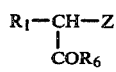     (VIA)

wherein Z is a reactive esterified hydroxyl group and $R_1$ and $R_6$ have the meanings given hereinabove or with a compound of the formula

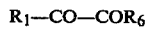     (VI)

wherein $R_1$ and $R_6$ have meanings given hereinabove, in the presence of a reducing agent, optionally with temporary protection of any primary and secondary amino groups and/or hydroxyl groups, which may be present; or (b) alkylating a compound of the formula

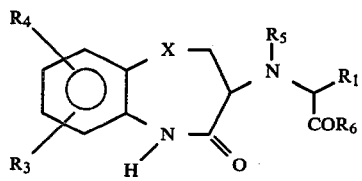     (VII)

in which the carboxylic ring may also be hexahydro and wherein X, $R_1$, $R_3$, $R_4$ and $R_5$ have the meanings given herein above with a compound of the formula

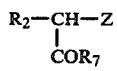     (VIB)

wherein Z is a reactive esterified hydroxyl group and $R_2$ and $R_7$ have the meanings given herein above, optionally while protecting temporarily any primary and secondary amino groups and/or hydroxyl groups which may be present; or (c) condensing a compound of the formula

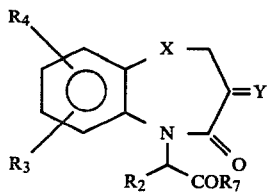     (VIII)

in which the carbocyclic ring may also be hexahydro and wherein Y is oxo or a reactive esterified hydroxyl group Z together with hydrogen, and X, $R_2$-$R_4$ and $R_7$ have the meanings given herein above, is condensed with an amine of the formula

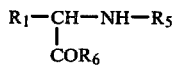     (IX)

wherein $R_1$, $R_5$ and $R_6$ have the meanings given herein above, with the proviso that when Y is oxo, the condensation is carried out in the presence of a reducing agent; or (d) solvolyzing a compound of the formula

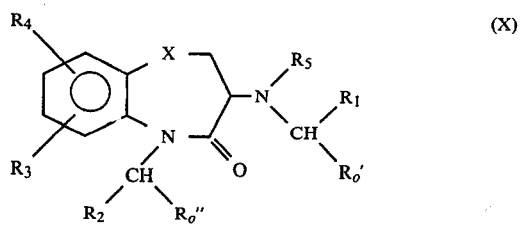     (X)

in which the carbocyclic ring may also be hexahydro and wherein X and $R_1$ to $R_5$ have the meanings given herein above, one of the symbols $R_o'$ and $R_o''$ is cyano and the other one is cyano, $COR_6$ or $COR_7$ as defined herein above;

(e) cyclizing a compound of the formula

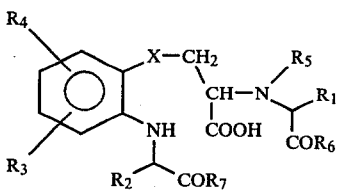     (XI)

in which the carbocyclic ring may also be hexahydro and wherein X, $R_1$ to $R_7$ have the meanings given herein above, or a reactive ester thereof; optionally with temporary protection of any primary and secondary amino groups and/or hydroxyl groups, which may be presents; or (f) cyclizing a compound of the formula

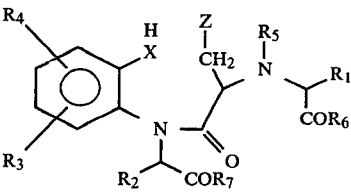     (XII)

in which the carbocyclic ring may also be hexahydro and wherein X and $R_1$ to $R_7$ have the meanings given herein above, and Z is a reactive esterified hydroxyl; or wherein $R_1$ to $R_4$, $R_6$ and $R_7$ have the meanings given above, and $R_5$ and Z combined represent a direct bond, optionally with temporary protection of any primary and secondary amino groups and/or hydroxyl groups which may be present; and if required alkylating the resulting compound of formula I wherein $R_5$ is hydrogen to obtain a compound of formula I wherein $R_5$ is lower alkyl; or (g) if desired, converting a resulting compound of formula I as specified above into another compound of formula I within its above-specified scope, and/or (h) if desired, converting a resulting compound of formula I as specified above and having salt-forming properties into a salt thereof or liberating a free compound from such a salt, and/or (j) if so required, obtaining an optical isomer which has a specific configuration with respect to at least one center of chirality from a mixture of stereoisomeric forms of a resulting compound of formula I.

In the above-cited processes, Z is a reactive esterified hydroxyl group, such as a hydroxyl group esterified with a strong organic acid, e.g. an aliphatic or aromatic sulfonic acid (such as a lower alkanesulfonic acid, especially methanesulfonic, trifluoromethanesulfonic acid, especially benzenesulfonic, p-toluenesulfonic, p-bromobenzenesulfonic and p-nitrobenzenesulfonic acid) or with a strong inorganic acid, such as, especially, sulfuric acid, or a hydrohalic acid, such as hydrochloric or, most preferably, hydriodic or hydrobromic acid. The alkylation is carried out under conventional general conditions at temperatures ranging between about 0° C. up to the boiling temperature of the reaction mixture, preferably at temperatures between room temperature to about 100° C. The reaction takes place advantageously in the presence of a solvent which is inert with respect to the reactants, such as a chlorinated lower alkane (e.g. chloroform or methylene chloride), an acyclic or cyclic ether (e.g. diethyl ether, 1,2-dimethoxyethane, dioxane or tetrahydrofuran) and, in particular, a low molecular weight tertiary amide (e.g. N,N-dimethylformamide, N,N-dimethylacetamide, N-methylpyrrolidone, N-ethylpiperidone and hexamethylphosphoric acid triamide). Advantageously, the strong acid HZ liberated during the reaction is bound by the addition of an acid-binding agent, such as, preferably, an inorganic acid-scavenger such as an alkali metal bicarbonate, carbonate or hydroxide, an organic quaternary ammonium salt (e.g. a tetrabutylammonium salt) or an organic tertiary base, such as triethylamine, N-ethylpiperidine, pyridine or quinoline.

In process (a), the alkylation can also be carried out under the conditions of reductive alkylation in the manner generally known and used in the art. In carrying out the alkylation, a compound of the general formula

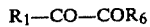

$$R_1-CO-COR_6 \quad (VI)$$

in which $R_1$ and $R_6$ have the meanings given herein above, is reacted with the starting bicyclic compound V and, simultaneously or in a subsequent step, with a reducing agent. Among reducing agents which are used simultaneously with the alkylating agent, mention should be made of catalytically activated hydrogen and complex metal hydrides such as sodium cyanoborohydride; among reducing agents used predominantly in a separate subsequent operation i.e. reduction of a preformed imine (Schiff's base), mention should be made of catalytically activated hydrogen, diborane and complex metal hydrides, such as, sodium cyanoborohydride which are added to the primary reaction mixture without isolating an intermediate, e.g. the imine. In this case, the alkylation is carried out advantageously in an organic solvent inert to the reducing agent, such as in an aliphatic or cyclic ether (such as diethyl ether, diisopropyl ether, 1,2-dimethoxyethane, dioxane or tetrahydrofuran) or an aliphatic alcohol (such as methanol, ethanol, isopropyl alcohol, glycol, glycol mono methyl ether or diethyleneglycol) or acetonitrile, preferably at about 0°-80° C. When the reducing agent, is catalytically activated hydrogen, the catalysts are those conventionally used as hydrogenation catalysts, i.e. preferably those of the class of precious metals (such as palladium, platinum and rhodium) on a carrier (such as calcium carbonate, aluminum oxide or barium sulfate), in a finely dispersed suspension without carrier or, in form of complexes, in a homogeneous phase. Also, finely dispersed transition metals such as Raney metals, especially Raney nickel, are very suitable catalysts for the reductive alkylation. The specific reaction conditions depend, to a large extent, on the particular hydrogenation catalyst and its precise activity, and do not differ from those generally known for hydrogenation. Temperatures ranging from room temperature to about 150° C., and pressures of hydrogen ranging from atmospheric pressure to about 300 atmospheres are applicable according to the standard procedures of the art. In addition to the inert solvents which were mentioned above in connection with the hydride reduction, low molecular weight amides, especially tertiary amides (such as N,N-dimethylformamide, N,N-dimethylacetamide, N-methylpyrrolidone, N-ethylpiperidone, hexamethylphosphoric acid triamide), and also formamide and acetamide can be used as suitable solvents.

The preformed imines referred to above are preferably prepared by condensing an amine of formula V with a carbonyl compound of formula VI in an inert solvent, e.g. toluene or methylene chloride, advantageously in the presence of a dehydrating catalyst, e.g. boron trifluoride etherate, p-toluenesulfonic acid, molecular sieves, or di-n-butyltin dichloride.

More specifically, the condensation of intermediates of formula V with the known alpha-ketoacid derivatives of formuls VI (e.g. chem. Ber. 31, 551, 3133) by reductive N-alkylation, optionally on the preformed imine, is carried out advantageously with an alkali metal cyanoborohydride such as sodium cyanoborohydride. The reductive alkylation with an alkali metal cyanoborohydride is preferably carried out in an inert solvent, e.g. methanol or acetonitrile, advantageously in the presence of an acid, e.g. hydrochloric acid, or acetic acid at a temperature between about 0° and 50°, preferably room temperature.

Process (b) is preferably carried out in the presence of very strong bases, such as alkali metal hydroxides (e.g. potassium hydroxide), alkali metal hydrides (e.g. sodium or potassium hydride), alkoxides (e.g. sodium methoxide or ethoxide, potassium tert-butoxide) or amides (e.g. lithium diisopropylamide), using ethers and amides mentioned above as preferred solvents. Alternately the said alkylation may be carried out under conditions of phase transfer catalysis, e.g. with an alkali metal hydroxide such as potassium hydroxide in the presence of a quaternary ammonium salt, e.g. tetrabutylammonium bromide, advantageously at room temperature.

The starting materials of formula VI, VIA and VIB, the alkylating agents, are known (e.g. Chem. Ber. 31, 551, 3133), or, if they are unknown, can be simply obtained by conventional synthetic processes.

The starting materials of formula V and VII can be obtained by conventional synthetic processes, and advantageously in the manner which is described in more detail and exemplified for specific intermediates hereinafter.

Process (c), also being an alkylation reaction is performed according to the same general considerations and under the same experimental conditions as the above processes (a) and (b) as described in detail above (i.e. substitutive alkylation or reductive alkylation). Starting materials of formula VIII can be obtained by conventional processes known per se, e.g. in the manner described more specifically hereinafter. The amines of formula IX are known, or if unknown, they are easily accessible by conventional synthetic methods.

The starting materials of formula IX represent amino acids and derivatives well known to the art. It is noteworthy that the optically active compounds of this invention may be synthesized starting with an optically active compound of formuls IX, e.g. L-alpha-aminophenylbutyric acid, L-phenylalanine and derivatives thereof.

Process (d) is also carried out in a conventional manner under the general conditions of solvolysis, which are known to convert cyanides (nitriles) into free carboxylic acids or their salts, esters or amides. For conversion into a free acid, hydrolysis with water is carried out advantageously in an inert organic solvent which is at least partially miscible with water, such as an ether (e.g. diethyl or diisopropyl ether, 1,2-dimethoxyethane or, especially dioxane or tetrahydrofuran) or a lower alkanol (e.g. methanol, ethanol, isopropyl alcohol, a butyl alcohol, especially tert-butyl alcohol), a larger amount of water being required in the latter cases in order to prevent alcoholysis. The hydrolysis can be catalysed both by strong acids, especially inorganic acids such as sulfuric acid or, preferably hydrohalic acids (e.g. hydrobromic or, as a first choice, hydrochloric acid), or by bases, especially inorganic bases such as hydroxides and carbonates of alkali metals, e.g. sodium and potassium hydroxide. The bases are usually employed in at least stoichiometric quantities giving rise to carboxylic acid salts as primary products. The acidic catalysts are advantageously applied as dilute aqueous solution for the best result. Final products of formula I, in which $COR_6$ and/or $COR_7$ represent an esterified carboxyl group, can be obtained by carrying out the solvolysis of the nitrile with the corresponding alcohol (alcoholysis) in the presence of a catalytic amount of an anhydrous strong acid, advantageously gaseous hydrogen chloride. Usually, excess alcohol is used as solvent; however, inert organic solvents can be added, such as acyclic and cyclic ethers (especially these mentioned above), and/or halogenated lower alkanes (especially chloroform and dichloromethane). If the alcoholysis is carried out under strictly anhydrous conditions, the primary product (imido ester) is to be hydrolyzed, advantageously by adding water to the reaction mixture; otherwise, by carrying out the alcoholysis in the presence of an approximately stoichiometric equivalent of water, the desired ester is obtained directly. In order to obtain a corresponding amide (i.e. a compound of formula I, wherein $COR_6$ and/or $COR_7$ is carbamoyl), a corresponding nitrile of formula X can preferably be subjected to alkaline hydrolysis in the presence of hydrogen peroxide.

The starting materials of formula X can be obtained by conventional methods known per se, e.g. by a condensation analogous to that of processes (a), (b) and (c) in which the reactants of e.g. formulae VIA, VIB and IX may be replaced with the corresponding nitriles, e.g. $R_2$—CH(Z)CN, $R_1$—CH(Z)CN and $R_5$NHCH($R_1$)CN respectively.

The cyclization according to process (e) can also be carried out in the manner known per se, e.g. by dehydration. Especially useful general methods for this purpose are those developed in connection with the formation of the amide bond in peptides, as reviewed in e.g. Houben-Weyl, Volumes 15/1 and 15/2 as cited hereinabove. According to one preferred modification, the amino group to be cyclized is rendered inactive by protonation (i.e. in the form of an acid addition salt), and the carboxyl group is converted into an activated ester, such as that with 2,4,5-trichlorophenol, pentachlorophenol, pentafluorophenol, 2-nitrophenol or, especially, 4-nitrophenol, or with an N-hydroxy compound, such as N-hydroxysuccinimide, 1-hydroxybenzotriazole or N-hydroxypiperidine, The cyclization is effected by basification preferably by the addition of an organic base, for example a quaternary ammonium salt, or especially a tertiary amine, such as triethylamine, N-ethylmorpholine or N-methylpiperidine, in order to reactivate the amino group to be cyclized by converting it into the unprotonated form. The reaction temperature is usually from $-20°$ to $+50°$ C., preferably approximately at room temperature, and customary solvents are used, for example, dioxan, tetrahydrofuran, acetonitrile, pyridine, dimethylformamide, dimethylacetamide, dimethyl-sulfoxide, N-methylpyrrolidone, hexamethylphosphoric acid triamide, as well as chloroform and methylene chloride, and expedient mixtures thereof. In a special variant of the process, the carboxy group can be directly activated in situ by the action of the free acid with a carbodiimide, such as N,N'-dicyclohexylcarbodiimide (optionally with the addition of N-hydroxysuccinimide, an unsubstituted or, for example, halogen-, methyl- or methoxy-substituted 1-hydroxybenztriazole or 4-hydroxybenzo-1,2,3-triazine-3-oxide or N-hydroxy-5-norbornene-2,3-dicarboximide), or with N,N'-carbonyldiimidazole.

Starting materials of formula XI may be obtained according to general methods known per se, e.g. from a starting material of formula XIII, or an ester derivative thereof,

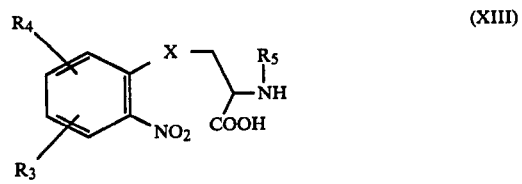

(XIII)

wherein X, $R_3$, $R_4$ and $R_5$ are as defined above, using the following sequence; alkylation in a manner similar to process (a) described hereinabove with a compound of the formula VI or VIA, reduction of the nitro group and subsequent alkylation of the corresponding aniline with a compound of formula VIB under conditions well known to the art.

The starting material of formula XIII may in turn be prepared by condensation of o-fluoronitrobenzene with a compound of the formula HX—CH$_2$CH(NHR$_5$)—COOH, wherein X and $R_5$ have meaning as defined above, optionally in optically active form, and wherein the amino group is in protected form, followed by removal of the protecting group as described herein.

The cyclization according to process (f) may be carried out under standard alkylating conditions e.g. as described under process (b).

The starting material of formula XII may be prepared by alkylating an intermediate of formula XIV

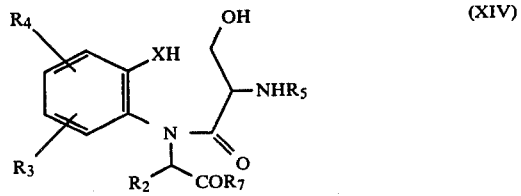

(XIV)

wherein $R_2$, $R_3$, $R_4$, $R_5$, $R_7$ and X have meaning as previously defined, and wherein the hydroxyl group is preferably in temporary protected form, with a compound of the formula VI or VIA in a manner similar to alkylation process (a) described herein above.

The starting material of formula XIV may be prepared by alkylating and acylating a compound of the formula XV

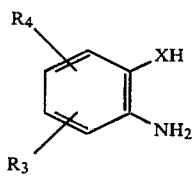
(XV)

wherein R₃, R₄ and X have meaning as defined above and wherein the group XH is in protected form, by methodology well-known in the art.

The intermediates of formula V for process (a) above are advantageously prepared as follows and as described in the examples herein.

(1) reducing the nitro group in a compound of formula XIII hereinabove, wherein the amino group NHR₅ is preferably in protected acylated form, preferably with zinc in acetic acid;

(2) cyclizing the resulting amino acid, which may also be prepared as described in J. Org. Chem. 23, 1251 (1958), in form of a functional derivative thereof, or in the presence of a condensing agent, e.g. dicyclohexylcarbodiimide, 1-dimethylaminopropyl-3-ethylcarbodiimide or 1,1'-carbonyldiimidazole;

(3) alkylating the resulting lactam of the formula

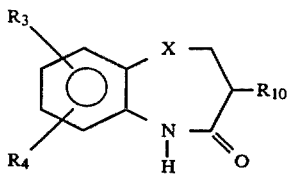
(XVI)

wherein R₃, R₄ and X have meaning as previously described and R₁₀ is amino, lower alkylamino, acyl-lower alkylamino, or acylamino, e.g. lower alkanoylamino or benzyloxycarbonylamino, with a compound of formula VIB under conditions described above under process (b), advantageously in the presence of an alkali metal hydroxide and a quaternary ammonium salt such as tetrabutylammonium bromide; and, if present (4) removing the amino protecting group.

The amines of formula V may also be prepared from compounds of general formula XVI wherein R₁₀ represents hydrogen, which are known per se or can be made by methods well known to the art, e.g. by ring expanding a ketone of the formula XVII

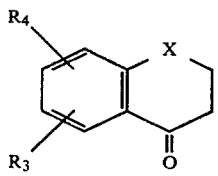
(XVII)

wherein R₃, R₄ and X have meaning as previously defined, with hydrazoic acid under conditions of the Schmidt rearrangement, or ring expanding an oxime of said ketone of formula XVII under conditions of the Beckmann rearrangement, e.g. with polyphosphoric acid. Said lactams (of formula XVI wherein R₁₀ is hydrogen) are alkylated with a compound of formula VIB under conditions described above for process (b), converted, e.g. to the alpha-halolactam (representing an intermediate of formula VIII wherein Y represents a reactive esterified hydroxyl group together with hydrogen) with a halogenating agent such as phosphorus pentachloride, and further converted to a compound of formula V, e.g. with potassium phthalimide followed by hydrazine to give said compound of formula V wherein R₅=H.

In turn the intermediates of formula VII for process (b) are advantageously prepared by alkylating a compound of formula XVI wherein R₁₀ is amino or lower alkylamino, and R₃ and R₄ are as previously defined, with a compound of formula VI or VIA under conditions previously described hereinabove for process (a), and as specifically described in the examples.

The intermediates of formula VIII (process c) wherein Y is oxo may prepared as follows:

(1) alkylating a lactam of general formula XVI wherein R₁₀ represents hydrogen with a compound of formula VIB under conditions described above for process (b), (2) treating the resulting compound with e.g. phosphorus pentachloride; and (3) hydrolyzing the resulting alpha-dichlorolactam, e.g. according to the methodology described in Synthesis 1982, 667.

Certain intermediates of formula VIII may also be obtained by oxidizing intermediats of formula V (preferably when X represents O or SO₂) with e.g. t-butyl nitrite and m-chloroperbenzoic acid according to the methodology described in Tetrahedron Letters 1982, 1875.

In any of the above condensations with reactants wherein R₆ or R₇ represents hydroxy, it may be desirable to prepare an appropriate carboxylate salt, preferably in situ, before condensation with the desired intermediates cited above.

In performing the optional interconversions of a resulting final product of formula I, into another compound within the above-specified scope of formula I, transformations such as the following are carried out: an amino group is alkylated, and/or a free hydroxyl or carboxyl group is liberated from its esterified form by hydrolysis or hydrogenolysis and/or a hydroxyl or amino group is acylated and/or a free carboxyl is esterified, and/or the aromatic carboxylic ring in formula I is reduced to the hexahydro form, and/or the hexahydrocarbocyclic ring is dehydrogenated to the aromatic carbocyclic ring, and/or thio of the symbol X is oxidized to sulfinyl or sulfonyl. Said interconversions may also be carried out for any of the intermediates where applicable.

All these optional interconversions are carried out by well-known conventional methods. A lower alkyl group as represented by R₅ can be introduced into the final product of formula I, wherein R₅ is hydrogen, by an alkylation reaction, using any of the modifications discussed in detail in connection with process (a). Both substitutive and reductive alkylation can be employed, the former with alkyl halides, the latter with lower aliphatic aldehydes and ketones and e.g. catalytically activated hydrogen or, in the case of formaldehyde, advantageously with formic acid as the reducing agent. By the substitutive alkylation, lower alkyl groups can also be introduced into a carbamoyl group represented by symbol $COR_6$ and/or $COR_7$.

Conversion of esters and amides, e.g. compounds of Formula I wherein $R_6$ and/or $R_7$ is e.g. lower alkoxy, aryl-lower alkoxy, amino, mono- or di-(lower alkyl)amino to compounds of formula I wherein $R_6$ and/or $R_7$ represents hydroxy is advantageously carried out by hydrolysis with inorganic acids such as hydrohalic or sulfuric acid or with aqueous alkalies, preferably alkali metal hydroxides such as lithium or sodium hydroxide.

The selective conversion of esters, e.g. compounds of formula I wherein $R_6$ and/or $R_7$ represents alpha-aryl(-lower)alkoxy, e.g. benzyloxy to compounds of formula I wherein $R_6$ and/or $R_7$ represents hydroxy is advantageously carried out by hydrogenolysis using hydrogen in the presence of a catalyst, e.g. palladium.

Compounds of formula I wherein neither $R_6$ nor $R_7$ represents hydroxy may be converted to monocarboxylic acids of formula I wherein one of $R_6$ and $R_7$ is hydroxy. Such conversion is carried out by selective hydrolytic or hydrogenolytic procedures well known to the art and based on the chemical character of the $R_6$ and $R_7$ substituents.

A proper combination of the ester groups can be chosen in the earlier stages of the synthesis, or by a proper choice of starting materials and reactants, e.g. in process (a), a selectively removable ester group being introduced with a carboxyl which is to be liberated in the last stage.

Free carboxylic acids of formula I wherein $R_6$ and/or $R_7$ represent hydroxy or salts thereof may be esterified with the appropriate alcohols or reactive derivatives thereof well known to the art to give the corresponding mono- or bis-esters e.g. compounds of formula I wherein $R_6$ and/or $R_7$ is lower alkoxy, aryl-lower alkoxy, lower alkanoyloxymethoxy, or lower alkoxycarbonyl-lower alkoxy. Furthermore the free carboxylic acids may be converted via reactive intermediates to mono- or di-amides e.g. compounds of formula I wherein $R_6$ and/or $R_7$ represents amino, mono- or di-(lower)alkylamino.

Compounds of formula I wherein $R_6$ and/or $R_7$ is lower alkoxy may also, be amidized with e.g. ammonia, mono- or di-(lower)alkylamines to yield compounds of formula I wherein $R_6$ and/or $R_7$ represents unsubstituted, mono- or di-(lower)alkylamino.

The compounds of the invention e.g. of formula I wherein $X=S$ can be converted into the S-oxides, for example with hydrogen peroxide or organic peracids, such as lower peralkanoic or perbenzoic acids, e.g. peracetic or m-chloro-perbenzoic acid, or preferably with m-chloro-perbenzoic acid in a solvent such as methylene chloride, advantageously at temperatures near room temperature to obtain either sulfoxides (SO) or sulfones ($SO_2$) depending on the quantity of peracid used. Conversion to the sulfoxides (SO) may also be advantageously carried out with periodic acid, or a salt thereof, e.g. sodium periodate in a polar solvent, e.g. methanol at room temperature.

Certain terms used in the foregoing processes have the meanings as defined below.

A reactive esterified hydroxy group represents such esterified by a strong inorganic or organic acid, above all a hydrohalic acid, e.g. hydrochloric, hydrobromic or hydriodic acid, an aliphatic or aromatic sulfonic acid, e.g. methane sulfonic acid or p-toluenesulfonic acid.

With reference to any of the above processes, any of said reactions may be carried out with a starting material in "protected" form. The expression "protected" is understood to mean appropriately protecting the potentially reactive, e.g. carboxy, amino, hydroxy and other interfering substituents in accordance with protective techniques well known to the art, e.g. as illustrated below, such that interfering reactions are avoided, by protecting such substituents prior to the desired reaction and subsequently, if necessary, removing the protective groups to obtain the desired compounds, e.g. of formula I.

Thus a free hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl, or benzyl ethers.

Similarly, a free basic amino group bearing at least one hydrogen or nitrogen, may be protected in the form of easily cleaved amides, e.g. as an acyl derivative such as the benzyloxycarbonyl (carbobenzyloxy) or the t-butyloxycarbonyl derivatives, or any other easily removable N-protecting group as commonly used in peptide chemistry.

The acylation of both hydroxyl and amino groups is carried out in the usual way, preferably using a corresponding acid anhydride or halide.

In any of the alkylation processes, primary and secondary amino groups in starting materials, except for the amino group to be alkylated, are preferably in a temporarily protected form during the alkylation. Suitable protecting groups, as well as procedures for their introduction and removal are well known in the art, being elaborated in great detail in particular as general methods for the synthesis of peptides, cf. Houben-Weyl: Methoden der organishen Chemie; 4th edition, vol. 15/I and II. The narrower selection of the protecting groups depends on the specific purpose, it being necessary to take into account in particular the specific properties of the particular starting materials and the reaction conditions of the specific process. In the case of several functional groups to be protected, advantageous combinations can be selected. Preferably, for example, similar or, even better, identical amino protecting groups, are used both in the radicals $R_6$, $R_7$ and in the radical $R_1$ and are simultaneously removed following alkylation.

Suitable as amino-protecting groups are especially amino-protecting groups that can be removed by reduction, for example especially those of the benzyloxycarbonyl (carbobenzyloxy) type in which the benzyloxycarbonyl group may be substituted in the aromatic moiety by halogen atoms, lower alkoxy groups and/or lower alkyl radicals and, especially, by nitro groups, such as the p-chloro- and p-bromobenzyloxycarbonyl, p-methoxybenzyloxycarbonyl, p-methylbenzyloxycarbonyl and, especially, p-nitrobenzyloxycarbonyl group, or alternatively the isonicotinyloxycarbonyl group. An advantageous amino-protecting group is an ethoxycarbonyl group which carries in the $\beta$-position a silyl group substituted by three hydrocarbon radicals, such as triphenylsilyl, dimethyl-tert.-butylsilyl or, especially, trimethylsilyl. A $\beta$-(trihydrocarbylsilyl)-ethoxycarbonyl group of this type, such as a $\beta$-(tri-lower alkylsilyl)-ethoxycarbonyl group, for example, especially $\beta$-(trimethylsilyl)-ethoxycarbonyl, forms with the amino group to be protected a corresponding $\beta$-trihydrocarbylsilylethoxycarbonylamino group (for example the $\beta$-trimethylsilylethoxycarbonylamino group), which may be removed under very specific, very mild conditions by the action of fluoride ions.

It is also possible to use groups that can be removed by acidolysis, such as the tert-butoxycarbonyl groups and analogous groups, as well as those of the aralkyl type, such as benzhydryl, di-(4-methoxy)-benzhydryl and triphenylmethyl (trityl).

For the optional temporary protection of hydroxy groups, protecting groups may be used advantageously that can be removed by reduction, cf. the above-cited text (Houben-Weyl), and also groups that can be removed by acidolysis, such as 2-tetrahydropyranyl, tert-butoxycarbonyl. Preferred hydroxy-protecting groups that can be removed by reduction are, for example, benzyl groups that may be substituted in the aromatic moiety by halogen, lower alkyl, lower alkoxy and/or, especially, nitro, especially the 4-nitrobenzyl group. It is also possible to use acyl groups that can be removed under weakly basic conditions, such as formyl or trifluoroacetyl.

The subsequent removal of protecting groups in accordance with the invention depends on their nature and is carried out in each case in a conventional manner known per se taking into consideration the general properties of the derived product. If the protecting groups for amino, and hydroxy groups have been so selected that they can be removed under similar conditions (especially preferred here are the groups removable by acidolysis or, for amino and hydroxy, by reduction, that have already been given special mention), then all of these protecting groups are advantageously removed in a single operation; in special cases, however, it is possible to use different types of groups and remove each of them individually.

The groups that can be removed by reduction, especially those that contain halogenated lower alkyl radicals (for example 2,2,2-trichloroethyl radicals), isonicotinyl radicals (for example isonicotinyloxycarbonyl) and, especially, substituted benzyl radicals, especially 4-nitrobenzyl radicals of any kind, are preferably removed by reduction, e.g. hydrogenation or by zinc reduction, usually in the presence of an acid, preferably acetic acid, and with or without the addition of an inert organic solvent, usually at room temperature. The removal of a protecting group by acid hydrolysis (acidolysis) is carried out by means of e.g. hydrogen chloride, or trifluoroacetic acid, and in the case of acid-sensitive protecting groups chiefly by means of a lower aliphatic carboxylic acid, such as formic acid and/or acetic acid, in the presence of water and, optionally, a polyhalogenated lower alkanol or lower alkanone, such as 1,1,1,3,3,3-hexafluoropropan-2-ol or hexafluoroacetone. In this manner it is possible, for example, for an N-trityl group to be removed by an organic acid, such as formic acid, acetic acid, chloroacetic acid or trifluoroacetic acid, in aqueous or absolute trifluoroethanol as solvent (cf. German Offenlegungsschrift DT 2 346 147) or by aqueous acetic acid; for the tert-butoxycarbonyl group to be removed by trifluoroacetic acid or hydrochloric acid; and for the 2-(p-biphenylyl)-isopropoxycarbonyl group to be removed by aqueous acetic acid or, for example, by a mixture of glacial acetic acid, formic acid (82.8% strength) and water (7:1:2) or in accordance with the process in DT 2 346 147. The β-silylethyl ester groups are preferably removed by fluoride ion-yielding reagents, for example fluorides of quaternary organic bases, such as tetraethylammonium fluoride.

For protection of a carboxyl group by esterification, a carboxyl group can be reacted directly with a diazoalkane, especially diazomethane, or with a corresponding alcohol in the presence of a strong acid catalyst (e.g. sulfuric acid or an organic sulfonic acid) and/or a dehydrating agent (e.g. dicyclohexylcarbodiimide). Alternatively, the carboxyl group can be converted into a reactive derivative thereof, such as an active ester mentioned in connection with process (e), or into a mixed anhydride, e.g. with an acid halide (i.e., especially an acid chloride), and this activated intermediate reacted with the desired alcohol.

The free carboxyl group can be liberated from an esterified carboxyl in a manner generally known, especially by base-catalyzed hydrolysis. Of special interest, however, are methods capable of selectively liberating one particular carboxyl group represented by the symbols —$COR_6$ and —$COR_7$. In such a case, use can be made of a proper combination of ester groups known in the art especially as carboxyl-protecting groups and developed in a great variety in particular for the synthesis of peptides, cf. Houben-Weyl, Volumes 15/1 and 15/2 as cited hereinabove. Radicals suitable for selective removal with liberation of the carboxyl are esters derived, for example, from alcohols that yield radicals that can be removed by acidolysis, such as cyanomethyl alcohol, benzoylmethyl alcohol or tert-butyl alcohol, but especially alcohols that yield radicals which can be removed by reduction, such as 2,2,2-trichloroethanol, benzyl alcohol, and especially 4-nitrobenzyl alcohol, or alternatively isonicotinyl alcohol. An especially advantageous class of substituted alkanols are ethyl alcohols which carry in the β-position a tri-substituted silyl group, such as triphenylsilyl, dimethyl-tert-butylsilyl or, especially, trimethylsilyl. As is described, for example, in Belgian Pat. No. 851,576, these alcohols are particularly suitable for selective removal because the corresponding β-silylethyl esters, for example β-(trimethylsilyl)-ethyl esters, have the stability of customary alkyl esters but can selectively be removed under mild conditions by the action of fluoride ions while retaining other esterified carboxyl groups, for example alkoxycarbonyl groups.

The removal of esterifying groups depends on their nature and is carried out in each case in a conventional manner known per se taking into consideration the properties of the other radicals involved. The groups that can be removed by reduction, especially those that contain halogenated lower alkyl radicals (for example 2,2,2-trichloroethyl radicals), isonicotinyl radicals (for example isonicotinyloxycarbonyl) and, optionally substituted benzyl radicals, especially 4-nitrobenzyl radicals of any kind, are preferably removed by zinc reduction, usually in the presence of an acid, preferably acetic acid, and with or without the addition of an inert organic solvent, usually at room temperature, those of the benzyl type, especially unsubstituted benzyl esters, also by hydrogenolysis techniques conventionally used for benzyl groups.

The removal of an ester group by acid hydrolysis (acidolysis) can be carried out especially in the case of groups of the tert-butyl type, by means of hydrogen chloride, hydrogen fluoride or trifluoroacetic acid. The β-silylethyl ester groups are preferably removed by fluoride-ion-yielding reagents, for example fluorides of quaternary organic bases, such as tetraethylammonium fluoride. Ester groups that are base-unstable can be carefully removed by the rapid action of an aqueous sodium or potassium bicarbonate solution or, preferably, aqueous ammonia in an organic solvent, usually at room temperature. The ester groups are preferably removed under the reaction conditions of the examples, or under analogous conditions.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the number of asymmetric carbon atoms, as pure optical isomers, such as antipodes, or as mixtures of optical mixtures such as racemates or mixtures of diastereoisomers.

Resulting mixtures of diastereoisomers and mixtures of racemates can be separated on the basis of the physicochemical differences of the constituents, in known manner, into the pure isomers, diastereoisomers or racemates, for example by chromatography and/or fractional crystallisation.

Resulting racemates can furthermore be resolved into the optical antipodes by known methods, for example by recrystallisation from an optically active solvent, by means of microorganisms or by reacting an acidic end product with an optically active base that forms salts with the racemic acid, and separating the salts obtained in this manner, for example on the basis of their different solubilities, into the diastereoisomers, from which the antipodes can be liberated by the action of suitable agents. Basic racemic products can likewise be resolved into the antipodes, for example, by separation of diastereomeric salts thereof, e.g. by the fractional crystallization of d- or l-tartrates. Any racemic intermediates or starting materials can likewise be resolved.

Advantageously, the more active of the two antipodes is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of the invention wherein $COR_6$ and/or $COR_7$ represent carboxy can also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Compounds that have both a free carboxy group and a basic group may be in the form of inner salts and these are obtained, for example, by establishing the isoelectric point.

The compounds, including their salts, can also be obtained in the form of their hydrates, or include other solvents used for the crystallization.

The pharmaceutical compositions according to the invention are those suitable for enteral, such as oral or rectal, and parenteral administration to mammals, including man, for the treatment or prevention of diseases responsive to inhibition of angiotensin-converting enzyme, e.g. cardiovascular diseases such as hypertension and congestive heart failure comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 20 to 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mmHg. Optical rotations are measured at room temperature.

EXAMPLE 1

A toluene solution (80 ml) of 2.05 g of (3R)-amino-5-carbomethoxymethyl-2,3-dihydro-1,5-benzothiazepin- 4(5H)-one and 1.59 g of ethyl 4-phenyl-2-oxobutyrate is stirred under nitrogen and treated with 0.1 ml of distilled boron trifluoride etherate. The reaction is stirred overnight at room temperature and then concentrated to give 4.20 g of light orange oil. This oil is dissolved in 8 ml of methanol followed by the dropwise addition of 0.48 g of sodium cyanoborohydride in 15 ml of methanol. Glacial acetic acid (4.4 ml) is added and the reaction is stirred overnight at room temperature under nitrogen. The solvent is removed under reduced pressure and the residue is partitioned between 10 ml of cold aqueous saturated sodium carbonate and 20 ml of methylene chloride. The aqueous layer is separated and extracted with an additional 20 ml of methylene chloride. The organic portions are combined and dried over potassium carbonate. After concentration in vacuo, the residue is purified by flash chromatography on silica gel (1:1 ether-hexane as eluent) to afford (3R)-[N-(1-carboethoxy-3-phenylpropyl)amino]-5-carbomethoxymethyl-2,3-dihydro-1,5-benzothiazepin-4(5H)-one as a mixture of diastereomers; [alpha]$_D$= −175.7° (c=1.15, absolute ethanol); NMR (CDCl$_3$) δ4.95 (d of d, 1), 3.70 (s, 3), 1.20 and 1.09 (t, 3).

The starting material is prepared as follows:

A mixture of 67.8 g of N-acetyl-L-cysteine and 100.8 g of sodium bicarbonate in 300 ml of water is added to 55.4 ml of o-fluoronitrobenzene in 1 l of ethanol. The reaction is heated to reflux for 3 hr with mechanical stirring and allowed to cool to room temperature. After removing the solids by filtration, the solution is concentrated to one fourth of the original volume and diluted with 1 l of water. The aqueous suspension is washed with 200 ml of ether and acidified to pH 1 with 12N aqueous hydrochloric acid. The resulting yellow precipitate is collected by filtration and dried in vacuo at 70° C. over phosphoruos pentoxide to afford S-(o-nitrophenyl)-N-acetyl-L-cysteine; m.p. 175°–176° C.; [α]$_D$= +87.8° (c=1.15, absolute ethanol).

A solution of 71 g of S-(o-nitrophenyl)-N-acetyl-L-cysteine in 300 ml of 18M sulfuric acid and 1200 ml of water is heated to reflux for 30 min. The solution is cooled in ice and treated with 700 ml of concentrated ammonium hydroxide. The resulting solid is recrystallized from boiling water to afford S-(o-nitrophenyl)-L-cysteine; m.p. 168°–171° C.; [α]$_D$= +67.3° (c=1.1, 1N hydrochloric acid).

To a solution of 48.4 g of S-(o-nitrophenyl)-L-cysteine in 100 ml of 2N aqueous sodium hydroxide at 0° C. is added 28.8 ml of benzyl chloroformate and 50 ml of 4N aqueous sodium hydroxide simultaneously from two addition funnels. The mixture is mechanically stirred overnight at room temperature and then extracted with 150 ml of ether. The aqueous layer is separated and acidified to pH 1 with 12N aqueous hydrochloric acid. The resulting gummy yellow solid is stirred for 3 hr in 500 ml of water, collected by filtration, and dried overnight at 70° C. in vacuo to afford S-(o-nitrophenyl)-N-carbobenzyloxy-L-cysteine; m.p. 84°–88° C.; [α]$_D$= +46.6° (c=1.25, methanol).

A 5 l 3-neck flask fitted with a mechanical stirrer and condenser is charged with 62.1 g of S-(o-nitrophenyl)-N-carbobenzyloxy-L-cysteine, 17.6 g of ammonium chloride and 3 l of methanol. To this mixture is added 150 g of zinc dust. The reaction is heated for 4 hr at reflux and then stirred overnight at room temperature. The reaction is filtered through celite and the solids are further washed with 300 ml of boiling methanol. The methanol fractions are combined and concentrated. The residue is dissolved in 1200 ml of 1N hydrochloric acid and filtered through celite. The acidic solution is cooled to 0° C. and the pH is adjusted to 5 with saturated sodium acetate. The resulting white precipitate is collected and dried at 80° C. in vacuo to give S-(o-aminophenyl)-N-carbobenzyloxy-L-cysteine; m.p. 161°–162° C.; [α]$_D$= −5C° ((c=1.0, absolute ethanol).

A 500 ml flask is charged with 37.6 g of S-(o-aminophenyl)-N-carbobenzyloxy-L-cysteine, 236 ml of dimethylformamide and 20.8 g of 1-(3-dimethylaminopropyl)-3-ethylcarbodiimide hydrochloride. The reaction is stirred under nitrogen for 3 hr and then diluted with 940 ml of ethyl acetate. The solution is washed with 940 ml of 1N aqueous sodium bicarbonate and 4×940 ml of water. The organic phase is dried over magnesium sulfate and concentrated to a yellow solid. This is triturated with ether and dried in vacuo to give (3R)-carbobenzyloxyamino-2,3-dihydro-1,5-benzothiazepin-4(5H)-one; m.p. 178°–179° C.; [α]$_D$= −96.6° (c=0.99, chloroform).

A mixture of 9.84 g of (3R)-carbobenzyloxyamino-2,3-dihydro-1,5-benzothiaazepin-4(5H)-one, 2.16 g of powdered potassium hydroxide, 0.97 gm of tetrabutylammonium bromide and 60 ml of tetrahydrofuran is cooled to 0° C. and treated with 2.8 ml of methyl bromoacetate. This is added dropwise under nitrogen. The reaction is allowed to stir for 3 hr at room temperature. At this time, the insoluble materials are removed by filtration and the tetrahydrofuran is evaporated under reduced pressure. The residue is partitioned between 90 ml of ether and 30 ml of water and the organic phase is separated, washed with 25 ml of water, 25 ml of 0.5N aqueous hydrochloric acid and dried over magnesium sulfate. After concentration in vacuo, the crude material is triturated with 1:1 ether-hexane which affords (3R)-carbobenzyloxyamino-5-carbomethoxymethyl-2,3-dihydro-1,5-benzothiazepin-4(5H)-one. This is used without further purification in the following reaction; NMR (CDCl$_3$) δ 7.18 (s, 5), 4.95 (s, 2), 3.70 (s, 3), 2.80 (d of d, 1); IR (CCl$_4$) 3420 (NH), 1725 (C=O, ester), 1680 (C=O, lactam) cm$^{-1}$.

A mixture of 5.9 g of (3R)-carbobenzyloxyamino-5-carbomethoxymethyl-2,3-dihydro-1,5-benzothiazepin-4(5H)-one in 24 ml of 31% hydrogen bromide in acetic acid is allowed to stir 1 hr at room temperature. Then, 150 ml of ether is added and the resulting white precipitate is filtered and dissolved in 100 ml of saturated aqueous sodium bicarbonate. The aqueous solution is extracted with 3×60 ml of ethyl acetate. The combined organic extracts are dried over potassium carbonate and concentrated to afford (3R)-amino-5-carbomethoxymethyl-2,3-dihydro-1,5-benzothiazepin-4(5H)one; m.p. 114°–118° C.; [α]$_D$= −299.5° (c=0.6, absolute ethanol).

EXAMPLE 2

(3R)-[N-(1-carboethoxy-3-phenylpropyl)amino]-5-carbomethoxymethyl-2,3-dihydro-1,5-benzothiazepin-4(5H)-one (2.3 g) is dissolved in 8 ml of methanol and 5 ml of 1N aqueous sodium hydroxide. After stirring overnight, the reaction is concentrated to dryness. The resulting solid is dissolved in a minimum amount of water, extracted with an equal volume of ether and acidified to pH 4 with 2N aqueous hydrochloric acid. The acidic solution is then extracted with 2×50 ml of ethyl acetate. The organic extracts are combined and dried over magnesium sulfate. Removal of solvent affords (3R)-[N-(1-carboxy-3-phenylpropyl)amino]-5-carboxymethyl-2,3-dihydro-1,5-benzothiazepin-4(5H)-one; m.p. 114°–117° C.; [alpha]$_D$=−165.5° (c=1.0, methanol).

EXAMPLE 3

(a) A mixture of 1.1 g of (3R)-{N-[(1S)-carboethoxy-3-phenylpropyl]amino}-2,3-dihydro-1,5-benzothiazepin-4(5H)-one, 0.41 g of powdered potassium hydroxide and 0.092 g of tetrabutylammonium bromide in 40 ml of tetrahydrofuran is cooled to 0° C. and 0.40 g of bromoacetic acid is added. After stirring 3 hr at room temperature, the reaction is concentrated and the residue taken up in 30 ml of water. The aqueous solution is acidified to pH 6 with 2N aqueous hydrochloric acid. The product is extracted into ethyl acetate (100 ml) and dried over magnesium sulfate. After removal of solvents at reduced pressure, the product is dissolved in 20 ml of ether, cooled to 0° C. and treated with gaseous hydrogen chloride. A white precipitate forms and is collected by filtration and dried in vacuo to give (3R)-{N-[(1S)-carboethoxy-3-phenylpropyl]amino}-5-carboxymethyl-2,3-dihydro-1,5-benzothiazepin-4(5H)-one hydrochloride; m.p. 103° C. (decomp); [alpha]$_D$=−132.9° (c=0.35, absolute ethanol).

(b) Following the procedure for the above example, (3R)-{N-[(1R)-carboethoxy-3-phenylpropyl]amino}-2,3-dihydro-1,5-benzothiazepin-4(5H)-one affords (3R)-{N-[(1R)-carboethoxy-3-phenylpropyl]amino}-5-carboxymethyl-2,3-dihydro-1,5-benzothiazepin-4(5H)-one hydrochloride; m.p. 101° C. (decomp); [alpha]$_D$=−163.7° (c=0.3, absolute ethanol).

The starting materials are prepared as follows:

A mixture of 29.7 g of (3R)-carbobenzyloxyamino-2,3-dihydro-1,5-benzothiazepin-4(5H)-one in 105 ml of 31% hydrogen bromide in acetic acid is stirred for 1 hr at room temperature. Then 200 ml of ether is added. The resulting precipitate is collected by filtration, washed with an additional 100 ml of ether and then slowly added to 250 ml of saturated aqueous sodium bicarbonate. The aqueous phase is extracted with 3×100 ml of ethyl acetate and the organic extracts are combined and dried over magnesium sulfate. Concentration in vacuo gives a solid which is triturated with ether and dried at reduced pressure to give (3R)-amino-2,3-dihydro-1,5-benzothiazepin-4(5H)-one; m.p. 162°–166° C; [α]$_D$=−302.9° (c=1.1, methanol).

To a solution of 11.9 g of (3R)-amino-2,3-dihydro-1,5-benzothiazepin-4(5H)-one and 12.6 g of ethyl 4-phenyl-2-oxo butyrate in 120 ml of chloroform under nitrogen is added 0.75 ml of distilled boron trifluoride etherate. The reaction is stirred 18 hr at room temperature. It is then filtered and concentrated to give an orange oil. This material is dissolved in 200 ml of ethanol and treated with 4.17 g of sodium cyanoborohydride and 38 ml of glacial acetic acid. After stirring overnight under nitrogen, the solvent is removed under reduced pressure and the residue is dissolved in 200 ml of methylene chloride and washed with 2×100 ml of cold aqueous saturated sodium carbonate. The organic portion is dried over magnesium sulfate and concentrated to give a viscous oil; NMR (CDCl$_3$) δ 6.8–7.8 (m, 9), 3.8–4.5 (m, 2), 1.0–1.5 (m, 3); IR (neat) 3300 (NH), 1730 (C=O, ester), 1675 (C=O, lactam) cm$^{-1}$.

The diastereoisomers are separated by preparative NPLC on silica gel [solvent system, tetrahydrofuran, hexane (1:4)]. This affords (3R)-{N-[(1S)-carboethoxy-3-phenylpropyl]amino}-2,3-dihydro-1,5-benzothiazepin-4-(5H)-one; NMR (CDCl$_3$) δ 8.70 (s, 1), 6.90–7.80 (m, 9), 4.05 (q, 2), 1.18 (t, 3); IR (neat) 3300 (NH), 1725 (C=O, ester), 1670 (C=O, lactam) cm$^{-1}$; and of (3R)-{N-[(1R)-carboethoxy-3-phenylpropyl]amino}-2,3-dihydro-1,5-benzothiazepin-4(5H)-one; NMR (CDCl$_3$) δ 9.00 (s, 1), 6.90–7.70 (m, 9), 4.10 (q, 2), 1.18 (t, 3); IR (neat) 3300 (NH), 1730 (C=O, ester), 1675 (C=O, lactam) cm$^{-1}$.

EXAMPLE 4

A solution of (3R)- {N-[(1S)-carboethoxy-3-phenylpropyl]amino}-2,3-dihydro-1,5-benzothiazepin-4(5H)-one (1.05 g), 0.195 g of powdered potassium hydroxide and 0.087 g of tetrabutylammonium bromide in 10 ml of tetrahydrofuran is cooled to 0° C. and 0.25 ml of methyl bromoacetate is added dropwise. The reaction is stirred 3 hr at room temperature and filtered. The tetrahydrofuran is removed in vacuo. The residue is dissolved in 25 ml of ether and washed with 10 ml of water and 10 ml of 0.5N aqueous hydrochloric acid. After drying over magnesium sulfate, the crude material is purified by flash chromatography on silica gel [solvent system, ether, hexane (1:)] to afford (3R)-{N-[(1S)-carboethoxy-3-phenylpropyl]amino}-5-carbomethoxymethyl-2,3-dihydro-1,5-benzothiazepin-4(5H)-one; NMR (CDCl$_3$) δ 4.95 (d of d, 1), 3.70 (s, 3), 4.00 (q,2), 1.20 (t, 3); [alpha]$_D$=−145.3° (c=0.6, methanol).

EXAMPLE 5

Following the preceding example, starting with 1.04 g of (3R)-{N-[(1R)-carboethoxy-3-phenylpropyl]amino}-2,3-dihydro-1,5-benzothiazepin-4(5H)-one, (3R)-{N-[(1R)-carboethoxy-3-phenylpropyl]amino}-5-carbomethoxymethyl 2,3-dihydro-1,5-benzothiazepin-4-(5H)-one is obtained;

NMR (CDCl$_3$) δ 6.95–7.80 (m, 9), 4.90 (d of d, 1), 3.80 (s, 3), 1.20 (t, 3); IR (CCl$_4$) 1750 (C=O, ester), 1675 (C=O, lactam), 3350 (NH) cm$^{-1}$.

EXAMPLE 6

(3R)-{N-[(1S)-carboethoxy-3-phenylpropyl]amino}-5-carbomethoxymethyl-2,3-dihydro-1,5-benzothiazepin-4(5H)-one (0.512 g) is dissolved in 8 ml of methanol and 2.5 ml of 1N aqueous sodium hydroxide. After stirring overnight, the reaction is concentrated to dryness. The resulting solid is dissolved in a minimum amount of water, extracted with an equal volume of ether and acidified to pH 4 with 2N aqueous hydrochloric acid. This affords (3R)-{N-[(1S)-carboxy-3-phenylpropyl]amino}-5-carboxymethyl-2,3-dihydro-1,5-benzothiazepin-4(5H)-one; [α]$_D$=−176.3° (c=0.6, 1N aqueous sodium hydroxide); m.p. 216°–218° C.

EXAMPLE 7

Following the preceding example starting with 0.58 g of (3R)-{N-[(1R)-carboethoxy-3-phenylpropyl]amino}-5-carbomethoxymethyl-2,3-dihydro-1,5-benzothiazepin-4(5H)-one, (3R)-{N[(1R)-carboxy-3-phenylpropyl]amino}-5-carboxymethyl-2,3-dihydro-1,5-benzothiazepin-4(5H)-one is obtained; [alpha]$_D$=−201.6° (c=0.5, methanol); m.p. 140°–144° C.

EXAMPLE 8

A solution of 0.524 g of (3R)-amino-5-carbomethoxymethyl-2,3-dihydro-1,1-dioxo-1,5-benzothiazepin-4(5H)-one, 1.09 g of ethyl-2-oxo-4-phenylbutyrate and 0.133 g of sodium cyanoborohydride is stirred overnight at room temperature under nitrogen in 26 ml of 1:1 methanol-glacial acetic acid. The solvent is removed under reduced pressure and the residue is partitioned between 10 ml of cold saturated sodium carbonate and 40 ml of methylene chloride. The aqueous layer is separated and extracted with an additional 25 ml of methylene chloride. The organic extracts are combined and dried over potassium carbonate. The product is purified by flash chromatography on silica gel [solvent, acetone, hexane (3.7)] to afford (3R)-[N-(1-carboethoxy-3-phenylpropyl)-amino]-5-carbomethoxymethyl-2,3-dihydro-1,1-dioxo-1,5-benzothiazepin-4(5H)-one; NMR (CDCl$_3$) δ 6.90–8.20 (m, 10) 5.10 [d(shoulder), 1]3.80 (2, 3), 1.00–1.50 (m, 3); R$_f$ (40% acetone/hexane, silica gel)=0.40.

The starting material is prepared as follows:

To a solution of 4 g of (3R)-carbobenzyloxyamino-5-carbomethoxymethyl-2,3-dihydro-1,5-benzothiazepin-4(5H)-one in 40 ml of methylene chloride is added 1.68 g of sodium bicarbonate followed by 4.52 g of 80% m-chloroperoxybenzoic acid. The reaction is stirred overnight at room temperature under nitrogen, filtered and concentrated. The resulting semi-solid is triturated with ether to give (3R)-carbobenzyloxyamino-5-carbomethoxymethyl-2,3-dihydro-1,1-dioxo-1,5-benzothiazepin-4(5H)-one. This is contaminated with a small amount of m-chlorobenzoic acid but is suitable for use without further purification; IR (CCl$_4$)3420 (NH), 1695 (>N—C=O), 1340, 1160

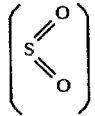

cm$^{-1}$; [α]$_D$=−94.0° (c=1.5, absolute ethanol).

A solution of 1.7 g of (3R)-carbobenzyloxyamino-5-carbomethoxymethyl-2,3-dihydro-1,1-dioxo-1,5-benzothiazepin-4(5H)-one in 8 ml of 31% hydrogen bromide in acetic acid is stirred 1 hr at room temperature and then diluted with 150 ml of ether. The resulting solid is isolated by filtration and added to 10 ml of saturated sodium bicarbonate. The product is extracted with 2×50 ml of ethyl acetate and dried over potassium carbonate. Concentration in vacuo gives (3R)-amino-5-carbomethoxymethyl-2,3-dihydro-1,1-dioxo-1,5-benzothiazepin-4(5H)-one; NMR (DMSO, d$_6$) δ 7.50–8.20 (m, 4), 4.45 (d of d, 2), 4.82 (s, 3), 2.42 (broad s, 2); IR (Nujol) 3300 (NH), 1725 (C=O, ester), 1660 (C=O, lactam) cm$^{-1}$.

EXAMPLE 9

(3R)-[N-(1-carboethoxy-3-phenylpropyl)amino]-5-carbomethoxymethyl-2,3-dihydro-1,1-dioxo-1,5-benzothiazepin-4(5H)-one (0.312 g) is dissolved in 5 ml of methanol and 1.3 ml of 1N aqueous sodium hydroxide and stirred overnight. The solvent is removed in vacuo and the solid residue is dissolved in a minimum amount of water. Acidification to pH 3 with 2N aqueous hydrochloric acid affords (3R)-[N-(1-carboxy-3-phenylpropyl)amino]-5-carboxymethyl-2,3-dihydro-1,1-dioxo-1,5-benzothiazepin-4(5H)-one hydrochloride; m.p. 190°–194° C. (decomp); [α]$_D$=−113.5° (c=0.2, methanol).

EXAMPLE 10

(a) A mixture of 0.74 g of (3R)-{N-[(1S)-carboxy-3-phenylpropyl]amino}-2,3-dihydro-1,5-benzothiazepin-4(5H)-one, 0.298 g of powdered potassium hydroxide, 0.067 g of tetrabutylammonium bromide and 30 ml of tetrahydrofuran is cooled to 0° C. and 0.2 ml of methyl bromoacetate is added dropwise. The reaction is stirred at room temperature for 3 hr. After filtration, the solvent is removed in vacuo to give a gummy residue which is dissolved in 30 ml of water. The solution is acidified to pH 6 with 2N aqueous hydrochloride acid. The product is extracted with 2×30 ml of ethyl acetate and dried over magnesium sulfate. The solvent is removed in vacuo to give a white solid which is dissolved in methylene chloride and treated with gaseous hydrogen chloride. Evaporation of the solvent affords (3R)-{N-[(1S)-carboxy-3-phenylpropyl]amino}-5-carbomethoxymethyl-2,3-dihydro-1,5-benzothiazepin-4(5H)-one hydrochloride; [α]$_D$=−102.2° (c=0.5, methanol); m.p. 90°–95° C.

(b) Similarly, starting with 0.37 g of (3R)-{N-[(1R)-carboxy-3-phenylpropyl]amino}-2,3-dihydro-1,5-benzothiazepin-4(5H)-one, (3R)-{N-[(1R)-carboxy-3-phenylpropyl]amino}-5-carbomethoxymethyl-2,3-dihydro-1,5-benzothiazepin-4(5H)-one hydrochloride is obtained; [α]$_D$=−119.6° (c=0.6, methanol); m.p. 66°–71° C.

The starting materials are prepared as follows:

(a) (3R)-{N-[(1S)-carboethoxy-3-phenylpropyl]amino}-2,3-dihydro-1,5-benzothiazepin-4(5H)-one (1.16 g) is stirred overnight at room temperature in 16 ml of methanol and 6 ml of 1N aqueous sodium hydroxide. The reaction mixture is concentrated and the resulting solid dissolved in 5 ml of water. After washing the aqueous layer with 2×5 ml of ether, (3R)-{N-[(1S)-carboxy-3-phenylpropyl]amino}-2,3-dihydro-1,5-benzothiazepin-4(5H)-one is obtained by acidification to pH 5.5 with 2N aqueous hydrochloric acid; [α]$_D$=−402.4° (c=0.5, 1N aqueous sodium hydroxide); m.p. 210°–213° (decomp).

(b) Similarly, beginning with 1.6 g of (3R)-{N-[(1R)-carboethoxy-3-phenylpropyl]amino}-2,3-dihydro-1,5-benzothiazepin-4(5H)-one (3R)-{N-[(1R)-carboxy-3-phenylpropyl]amino}-2,3-dihydro-1,5-benzothiazepin-4(5H)-one is obtained; [α]$_D$=−180.4° (c=1.05, methanol); m.p. 95°–100° C. (decomp).

EXAMPLE 11

To a solution of (3R)-{N-[(1S)-carboethoxy-3-phenylpropyl)amino}-5-carbomethoxymethyl-2,3-dihydro-1,5-benzothiazepin-4(5H)-one (0.266 g) in 5 ml of methanol cooled to 0° C. is added 0.122 g of sodium periodate in 1 ml of water. The reaction is stirred 72 hr at room temperature and filtered. The solvent is removed in vacuo and the residue dissolved in 10 ml of methylene chloride and dried over potassium carbonate. Removal of solvent under reduced pressure affords (3R)-{N-[(1S)-carboethoxy-3-phenylpropyl]amino}-5-carbomethoxymethyl-2,3-dihydro-1-oxo-1,5-benzothiazepin-4(5H)-one; NMR (CDCl$_3$) δ 6.60–8.00 (m, 9), 4.90 and 5.20 (d of d, 1), 3.72 and 3.78 (s, 3); IR (CCl$_4$) 3330 (NH), 1680 (>N—C=O). 1120 (S—O) cm$^{-1}$.

EXAMPLE 12

To a solution of 0.20 g of (3R)-{N-[(1S)-carboethoxy-3-phenylpropyl]amino}-5-carbomethoxymethyl-2,3-dihydro-1-oxo-1,5-benzothiazepin-4(5H)-one in 3 ml of methanol is added 0.86 ml of 1N aqueous sodium hydroxide. The reaction is stirred overnight at room temperature and concentrated in vacuo. The residue is dissolved in 2 ml of water and extracted with 5 ml of ether. The aqueous layer is then acidified to pH 4 with 2N aqueous hydrochloric acid. The product, (3R)-{N-[(1S)-carboxy-3-phenylpropyl]amino}-5-carboxymethyl-2,3-dihydro-1-oxo-1,5-benzothiazepin-4(5H)-one, is collected by filtration and dried in vacuo at 80° C.; m.p. 140°–143° C.; $[\alpha]_D = -87.2°$ (c=0.5, methanol).

EXAMPLE 13

To 7 ml of 31% hydrogen bromide in acetic acid is added 1.3 g of (3R)-[N-(1-carbomethoxy-5-carbobenzyloxyaminopentyl)amino]-5-carboethoxymethyl-2,3-dihydro-1,5-benzothiazepin-4(5H)-one and the solution is stirred for 1 hr. Then, 75 ml of ether is added and the gummy solid is filtered and dissolved in 10 ml of saturated aqueous sodium bicarbonate. The aqueous solution is extracted with 2×50 ml of ethyl acetate. The combined organic extracts are dried over potassium carbonate and concentrated to afford (3R)-[N-(1-carbomethoxy-5-aminopentyl)amino]-5-carboethoxymethyl-2,3-dihydro-1,5-benzothiazepin-4(5H)-one; NMR (CDCl$_3$) δ 6.68–7.40 (m, 4), 2.30–3.70 (m, 9), 1.25 (t, 3), 0.80–2.10 (m, 9); $[\alpha]_D = -142°$ (c=0.6, absolute ethanol).

The starting material is prepared as follows:

A mixture of 5.67 g of (3R)-carbobenzyloxyamino-2,3-dihydro-1,5-benzothiazepin-4(5H)-one, 1.17 g of powdered potassium hydroxide, 0.56 g of tetrabutylammonium bromide and 35 ml of tetrahydrofuran is cooled to 0° and treated with 1.9 ml of ethyl bromoacetate. This is added dropwise under nitrogen. The reaction is allowed to stir for 3 hr at room temperature. At this time, the insoluble materials are removed by filtration and the tetrahydrofuran is evaporated under reduced pressure. The residue is partitioned between 50 ml of ether and 15 ml of water and the organic phase is separated, washed with 15 ml of water, 15 ml of 0.5N aqueous hydrochloric acid and dried over magnesium sulfate. After concentration in vacuo, there remains a viscous oil which is purified by flash chromatography on silica gel [solvent system: acetone, hexane (1:4). This gives (3R)-carbobenzyloxyamino-5-carboethoxymethyl-2,3-dihydro-1,5-benzothiazepin-4(5H)-one; NMR (CDCl$_3$) δ 6.86–7.52 (m, 9), 4.85 (s, 2), 4.10 (q, 2), 2.75 (d of d, 1), 1.25 (t, 3); $[\alpha]_D = -246°$ (c=1.5, absolute ethanol).

A mixture of 3.0 g of (3R)-carbobenzyloxyamino-5-carboethoxymethyl-2,3-dihydro-1,5-benzothiazepin-4(5H)-one in 13 ml of 31% hydrogen bromide in acetic acid is allowed to stir 1 hr at room temperature. Then, 150 ml of ether is added and the resulting white precipitate is filtered and dissolved in 100 ml of saturated aqueous sodium bicarbonate. The aqueous solution is extracted with 3×60 ml of ethyl acetate. The combined organic extracts are dried over potassium carbonate and concentrated to afford (3R)-amino-5-carboethoxymethyl-2,3-dihydro-1,5-benzothiazepin-4(5H)-one; m.p. 103°–107°; $[\alpha]_D = -243°$ (c=0.65, absolute ethanol).

A mixture of 1.0 g of (3R)-amino-5-carboethoxymethyl-2,3-dihydro-1,5-benzothiazepin-4(5H)-one, 1.05 g of methyl 6-carbobenzyloxyamino-2-oxo-hexanoate, and 0.055 g of di-n-butyltin dichloride in 50 ml of toluene is heated to reflux for 3 hr using a Dean-Stark water separator. The reaction mixture is allowed to cool and is then concentrated in vacuo. The residue is dissolved in 8 ml of methanol and treated with a solution of 0.23 g of sodium cyanoborohydride in 9 ml of methanol followed by 2.2 ml of glacial acetic acid. The reaction is allowed to stir overnight at room temperature and then concentrated in vacuo. The residue is dissolved in 50 ml of methylene chloride, washed with cold saturated aqueous sodium carbonate and then dried over potassium carbonate. After concentration in vacuo there remains a gummy residue which is purified by flash chromatography on silica gel [solvent system: acetone, hexane (3:7)] to afford (3R)-[N-(1-carbomethoxy-5-carbobenzyloxyaminopentyl)amino]-5-carboethoxymethyl-2,3-dihydro-1,5-benzothiazepin-4(5H)-one as a 1:1 mixture of diastereomers; NMR (CDCl$_3$) δ 6.68–7.45 (m, 9), 4.82 (s, 2), 3.20 (q, 2), 1.18 (t, 3), 1.00–1.80 (m, 6); $[\alpha]_D = -152.7°$ (c=1.5, absolute ethanol).

EXAMPLE 14

A solution of 0.54 g of (3R)-[N-(1-carbomethoxy-5-aminopentyl)amino]-5-carboethoxymethyl-2,3-dihydro-1,5-benzothiazepin-4(5H)-one in 5 ml of methanol is treated with 2.6 ml of 1N aqueous sodium hydroxide. The reaction is allowed to stir overnight and is then concentrated in vacuo. The residue is dissolved in a minimum amount of water and the aqueous solution is washed with an equal volume of ethyl acetate and then acidified to pH 2 with 2N aqueous hydrochloric acid. The solution is concentrated under reduced pressure and the residue dissolved in the minimum amount of ethanol and filtered. The filtrate is cooled in ice and ether added to initiate crystallization. The product is collected on a buchner funnel and dried at room temperature in vacuo to give (3R)-[N-(1-carboxy-5-aminopentyl)amino]-5-carboxymethyl-2,3-dihydro-1,5-benzothiazepin-4(5H)-one dihydrochloride; m.p. 125°–130°; $[\alpha]_D = -119.8°$ (c=0.8, absolute ethanol).

EXAMPLE 15

An ice cold mixture of 81 mg of 3-[N-(1-carboethoxy-3-phenylpropyl)amino]-2,3-dihydro-1,5-benzoxazepin-4(5H)-one, 15 mg of powdered potassium hydroxide and 6.5 mg of tetrabutylammonium bromide in 3 ml of dry tetrahydrofuran is treated with 32 mg of methyl bromoacetate. The reaction is allowed to stir for 3 hr at room temperature. At this time the solution is filtered and concentrated and the residue is dissolved in 20 ml of ethyl acetate. This is washed with 5 ml of water and dried over potassium carbonate. Concentration under reduced pressure affords 3-[N-(1-carboethoxy-3-phenylpropyl)amino]-5-carbomethoxymethyl-2,3-dihydro-1,5-benzoxazepin-4(5H)-one; NMR (CDCl$_3$) δ 6.35–8.00 (m, 10), 4.30–4.80 (m, 3), 3.67 (s, 3), 1.20 (t, 3); IR (neat) 3300 (NH), 1730 (C=O, ester), 1685 (C=O, lactam) cm$^{-1}$.

The starting material 3-[N-(1-carboethoxy-3-phenylpropyl)amino]-2,3-dihydro-1,5-benzoxazepin-4(5H)-one, is prepared as shown.

To a stirred suspension of 18.7 g of phosphorous pentachloride in 60 ml of toluene is added 4.9 g of 2,3-dihydro-1,5-benzoxazepin-4(5H)-one in one portion and the mixture is warmed at a steady rate to a water bath temperature of 90° over 2 hr. The reaction is then heated at a bath temperature of 97° for 1 hr before concentration in vacuo. The resulting brown oil is added to 25 ml of saturated aqueous sodium carbonate and stirred for 3 hr. The resulting solid is collected by suction filtration and air dried overnight on the funnel. This solid is then suspended in 10 ml of ethanol and 0.5 ml of concentrated ammonium hydroxide is added. The suspension is stirred for 2 hr and the solid is collected by suction filtration. Drying at 50° in vacuo affords 3,3-dichloro-2,3-dihydro-1,5-benzoxazepin-4(5H)-one; m.p. 170°–174°; NMR (DMSO, d$_6$) δ 6.72–7.40 (m, 5), 4.63 (s, 2).

A mixture of 2.9 g of 3,3-dichloro-2,3-dihydro-1,5-benzoxazepin-4(5H)-one, 30 ml of glacial acetic acid, 2.2 g of anhydrous sodium acetate and 86 mg of 5% palladium on charcoal is hydrogenated at atmospheric pressure for 45 min. The suspension is filtered through celite and the solids are washed with 5 ml of acetic acid. Concentration of the filtrate under reduced pressure affords a brown solid which is stirred in 17 ml of water for 30 min. The resulting solid is collected by vacuum filtration, washed with water and dried at 50° in vacuo to afford 3-chloro-2,3-dihydro-1,5-benzoxazepin-4,(5H)-one; m.p. 117°–121°; NMR (DMSO, d$_6$) δ 10.07 [s(broad), 1], 6.93 (s, 4), 4.00–5.05 (m, 3).

A mixture of 0.989 g of 3-chloro-2,3-dihydro-1,5-benzoxazepin-4(5H)-one and 1.0 g of potassium phthalimide in 5 ml of dimethylformamide is warmed to 90° overnight. The reaction mixture is poured into 20 ml of water and stirring is continued for 1 hr. Isolation by vacuum filtration and drying at 60° in vacuo affords 3-phthalimido-2,3-dihydro-1,5-benzoxazepin-4(5H)-one; m.p. 188°–193°; NMR (DMSO, d$_6$) δ 7.95 (s, 4), 6.61–7.40 (m, 5), 4.92 (d of d, 1), 4.01 (d, 2).

A suspension of 1.85 g of 3-phthalimido-2,3-dihydro-1,5-benzoxazepin-4(5H)-one in 60 ml of absolute ethanol is treated with 0.31 ml of hydrazine hydrate and the reaction mixture is heated to reflux for 1.5 hr. After cooling to room temperature, the solid is removed by filtration and the filtrate is concentrated in vacuo. The residue is dissolved in chloroform and filtered and concentrated a second time to afford 3-amino-2,3-dihydro-1,5-benzoxazepin-4(5H)-one; m.p. 65°–70°; NMR (CDCl$_3$) δ 6.50–7.60 (m, 4), 3.60–5.30 (m, 3), 3.25 [d (broad), 1].

The 3-amino-2,3-dihydro-1,5-benzoxazepin-4(5H)-one (0.250 g) is dissolved in 5 ml of methanol and 2.88 g of ethyl 2-oxo-4-phenylbutyrate is added. This is followed by the addition of a solution of 88 mg of sodium cyanoborohydride in 3 ml of methanol and 0.8 ml of glacial acetic acid. The reaction is stirred overnight under nitrogen and concentrated. The residue is dissolved in 20 ml of methylene chloride and washed with 10 ml of cold saturated sodium carbonate. After drying over magnesium sulfate the solution is concentrated to an oil which is purified by flash chromatography on silica gel [solvent, acetone, hexane (1:4)] to afford 3-[N-(1-carboethoxy-3-phenylpropyl)amino]-2,3-dihydro-1,5-benzoxazepin-4(5H)-one; NMR (CDCl$_3$) δ 9.35 (s (broad, 1], 6.50–7.30 (m, 10, 4.10 (q, 2), 2.67 (t (broad), 2], 1.21 (t, 3); IR (neat) 3220 (NH), 1730 (C═O, ester), 1685 (C═O, lactam) cm$^{-1}$.

The starting 2,3-dihydro-1,5-benzoxazepin-4(5H)-one is prepared according to J. Chem. Soc. 1965, 1140.

EXAMPLE 16

A mixture of 59 mg of 3-[N-(1-carboethoxy-3-phenylpropylamino]-5-carbomethoxymethyl-2,3-dihydro-1,5-benzoxazepin-4(5H)-one and 0.26 ml of 1N aqueous sodium hydroxide is stirred overnight in 2 ml of methanol. The solvent is removed in vacuo and the residue acidified with 0.5N aqueous hydrochloric acid to pH 2 to afford 3-[N-(1-carboxy-3-phenylpropyl)amino]-5-carboxymethyl-2,3-dihydro-1,5-benzoxazepin-4(5H)-one hydrochloride; NMR (DMSO,-d$_6$) δ 5.96–9.00 (m, 13), 4.80–5.20 (m, 1), 3.00–3.90 (m, 3), 1.70–2.40 (m, 2); IR (nujol) 3600–3100 (NH, OH), 1720 (C═O, acid), 1680 (C═O, lactam) cm$^{-1}$.

EXAMPLE 17

An ice cold mixture of 84 mg of 3-[N-(1-carboethoxy-3-phenylpropyl)amino]-5-methyl-1,3,4,5-tetrahydro-1,5-benzodiazepin-2-one, 15 mg of powdered potassium hydroxide and 6.5 mg of tetrabutylammonium bromide in 3 ml of dry tetrahydrofuran is treated with 32 mg of methyl bromoacetate. The reaction is allowed to stir for 3 hr at room temperature. At this time, the solution is filtered and concentrated and the residue dissolved in 20 ml of ethyl acetate. This is washed with 5 ml of water and dried over potassium carbonate. Concentration under reduced pressure affords 3-[N-(1-carboethoxy-3-phenylpropyl)amino]-1-carbomethoxymethyl-5-methyl-1,3,4,5-tetrahydro-1,5-benzo diazepin-2-one.

The starting material, 3-[N-(1-carboethoxy-3-phenylpropyl)amino]-5-methyl-1,3,4,5-tetrahydro-1,5-benzodiazepin-2-one, is prepared as shown.

To a stirred suspension of 18.7 g of phosphorous pentachloride in 60 ml of toluene is added 5.29 g of 5-methyl-1,3,4,5-tetrahydro-1,5-benzodiazepin-2-one in one portion and the mixture is warmed at a steady rate to a water bath temperature of 90° over 2 hr. The reaction is then heated at a bath temperature of 97° for 1 hr before concentration in vacuo. The residue is added to 25 ml of saturated aqueous sodium carbonate and stirred for 3 hr. The product is collected by filtration and air dried. This material is suspended in 10 ml of ethanol and 0.5 ml of concentrated ammonium hydroxide is added. The suspendion is stirred for 2 hr and the 3,3-dichloro-5-methyl-1,3,4,5-tetrahydro-1,5-benzodiazepin-2-one is collected.

A mixture of 3.06 g of 3,3-dichloro-5-methyl-1,3,4,5-tetrahydro-1,5-benzodiazepin-2-one, 30 ml of glacial acetic acid, 2.2 g of anhydrous sodium acetate and 86 mg of 5% palladium on charcoal is hydrogenated at atmospheric pressure until the theoretical amount of hydrogen has been absorbed. The suspension is filtered through celite and the solids are washed with 5 ml of acetic acid. Concentration of the filtrate and treatment of the residue with 17 ml of water for 30 min. affords 3-chloro-5-methyl-1,3,4,5-tetrahydro-1,5-benzodiazepin-2-one.

A mixture of 1.05 g of 3-chloro-5-methyl-1,3,4,5-tetrahydro-1,5-benzodiazepin-2-one and 1.0 of potassium phthalimide is warmed to 90° overnight. The reaction mixture is poured into 20 ml of water and stirring is continued for 1 hr. Isolation and drying affords 3-phthalimido-5-methyl-1,3,4,5-tetrahydro-1,5-benzodiazepin-2-one.

A suspension of 1.93 g of 3-phthalimido-5-methyl-1,3,4,5-tetrahydro-1,5-benzodiazepin-2-one in 60 ml of absolute ethanol is treated with 0.31 ml of hydrazine hydrate and the reaction mixture is heated to reflux for 1.5 hr. After cooling at room temperature, the solid is removed by filtration and the filtrate is concentrated in vacuo. The residue is dissolved in chloroform and filtered and concentrated again to afford 3-amino-5-methyl-1,3,4,5-tetrahydro-1,5-benzodiazepin-2-one.

The 3-amino-5-methyl-1,3,4,5-tetrahydro-1,5-benzodiazepin-2-one (0.267 g) is dissolved in 5 ml of methanol and 0.288 g of ethyl 2-oxo-4-phenylbutyrate is added. This is followed by the addition of a solution of 88 mg of sodium cyanoborohydride in 3 ml of methanol and 0.8 ml of glacial acetic acid. The reaction is stirred overnight under nitrogen and concentrated. The residue is dissolved in 20 ml of methylene chloride and washed with 10 ml of cold saturated sodium carbonate. After drying over magnesium sulfate the solution is concentrated and the residue purified to give 3-[N-(1-carboethoxy-3-phenylpropyl)amino]-5-methyl-1,3,4,5-tetrahydro-1,5-benzodiazepin-2(2H)-one.

The starting 5-methyl-1,3,4,5-tetrahydro-1,5-benzodiazepin-2-one is prepared according to J. Chem. Soc. 1965, 1140 from o-nitroaniline.

EXAMPLE 18

A mixture of 39 mg of 3-[N-(1-carboethoxy-3-phenylpropyl)amino]-1-carbomethoxymethyl-5-methyl-1,3,4,5-tetrahydro-1,5-benzodiazepin-2-one and 0.26 ml of 1N aqueous sodium hydroxide is stirred overnight in 2 ml of methanol. The solvent is removed in vacuo and the residue acidified to pH 2 with 0.5N aqueous hydrochloric acid to afford 3-[N-(1-carboxy-3-phenylpropyl)amino]-1-carboxymethyl-5-methyl-1,3,4,5-tetrahydro-1,5-benzodiazepin-2-one hydrochloride.

EXAMPLE 19

Preparation of 10,000 tablets each containing 10 mg of the active ingredient of Example 3:
Formula:

| | |
|---|---|
| (3R)-[N—(1-carboethoxy-3-phenylpropyl)amino]-5-carboxymethyl-2,3-dihydro-1,5-benzothiazepin-4(5H)-one hydrochloride | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 20

Preparation of an injectable formulation containing 25 mg of the active ingredient of Example 16 per 5 ml of solution:
Formula

| | |
|---|---|
| (3R)-[N—(1-carboethoxy-3-phenylpropyl)amino]-5-carboxymethyl-2,3-dihydro-1,5-benzoxazepin-4(5H)-one hydrochloride | 25.0 g |
| Propylparaben | 1.0 g |
| Water for injection q.s. | 5000.0 ml |

The active ingredient and preservative are dissolved in 3500 ml of water for injection and the solution is diluted to 5000 ml. The solution is filtered through a sterile filter and filled into injection vials under sterile conditions each vial containing 5 ml of the solution.

EXAMPLE 21

Preparation of 10,000 capsules each containing 20 mg of the active ingredient of Example 3.
Formula:

| | |
|---|---|
| (3R)-[N—(1-carboethoxy-3-phenylpropyl)amino]-5-carboxymethyl-2,3-dihydro-1,5-benzothiazepin-4(5H)-one hydrochloride | 200.00 g |
| Lactose | 1,700.0 g |
| Talcum powder | 100.0 g |

Procedure:

All the powders are passed through a screen with openings of 0.6 mm. Then the drug substance is placed in a suitable mixer and mixed first with the talcum, then with the lactose until homogenous. No. 3 capsules are filled with 200 mg; using a capsule filling machine.

Analogously, tablets, injectable formulations or capsules are prepared from the remaining compounds of the invention, e.g., those illustrated by the examples herein.

What is claimed is:

1. A compound of the formula

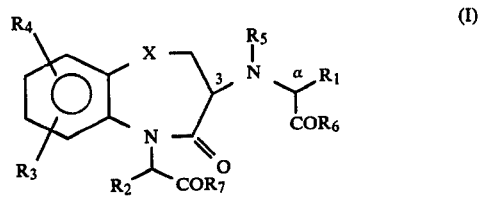

wherein
$R_1$ is hydrogen, lower alkyl, amino-lower alkyl, acylamino-lower alkyl, aryl, aryl-lower alkyl, cycloalkyl or cycloalkyl-lower alkyl;
$R_2$ is hydrogen or lower alkyl;
$R_3$ and $R_4$, each independently, represent hydrogen, lower alkyl, lowr alkoxy, lower alkanoyloxy, hydroxy, halogen or trifluoromethyl; or $R_3$ and $R_4$ taken together represent lower alkylenedioxy;
$R_5$ is hydrogen or lower alkyl;
$R_6$ and $R_7$ represent independently hydroxy; lower alkoxy; (amino, mono- or di-lower alkylamino)-substituted lower alkoxy; carboxy-substituted lower alkoxy; lower alkoxycarbonyl-substituted lower alkoxy; aryl-substituted lower alkoxy; (hydroxy, lower alkanoyloxy or lower alkoxy)-substituted lower alkoxy; (hydroxy, lower alkanoyloxy or lower alkoxy)-substituted lower alkoxymethoxy; bicyclo[2,2,1]-heptyloxycarbonyl-substituted lower alkoxy; 3-phthalidoxy; (lower alkyl, lower alkoxy, halo)-substituted 3-phthalidoxy; amino; lower alkylamino; di-lower alkylamino; pyrrolidino, piperidino or perhydroazepino; (amino or acylamino)-substituted lower alkylamino; α-(carboxy or lower alkoxycarbonyl)-substituted lower alkylamino; aryl-substituted lower alkylamino which can be substituted on the α-carbon by carboxy or lower alkoxycarbonyl;
X represents $S(O)_p$, N—$R_8$ or O, in which radicals $R_8$ represents hydrogen, lower alkyl or aryl, and p represents zero, one or two; and
wherein the carbocylic ring may also be hexahydro; and wherein within the above definitions acylamino represents lower alkanoylamino; lower alkoxycarbonylamino; aryl-lower alkanoylamino; aryl-lower alkoxycarbonylamino; or aroylamino in which aroyl represents benzoyl or benzoyl substituted by lower alkyl, lower alkoxy or halogen, or nicotinoyl; and wherein within the above definitions aryl represents phenyl unsubstituted or mono- or di-substituted by lower alkyl, lower alkoxy, lower alkylenedioxy, lower alkanoyloxy, hydroxy, halogen or trifluoromethyl; and cycloalkyl contains 3 to 8 carbons; or a pharmaceutically acceptable salt thereof.

2. A compound of claim 1 wherein $R_1$ is lower alkyl, amino-lower alkyl or aryl-lower alkyl; $R_2$ and $R_5$ independently represent hydrogen or lower alkyl;

$R_3$ and $R_4$ represent independently hydrogen, lower alkyl, lower alkoxy, lower alkanoyloxy, hydroxy, halogen or trifluoromethyl; or $R_3$ and $R_4$ taken together represent lower alkylenedioxy; $R_6$ and $R_7$ represent independently hydroxy, amino, mono- or di-lower alkylamino, lower alkoxy, benzyloxy, pyridylmethoxy, pivaloyloxymethoxy, bicyclo[2,2,1]heptyloxy-substituted methoxy, α-carboxyethoxy or α-lower alkoxycarbonylethoxy;

X represents O, $S(O)_p$ wherein p represents zero, 1 or 2, or N—$R_8$ wherein $R_8$ represents hydrogen or lower alkyl;

$R_6$ and $R_7$, have meaning as defined in said claim; and wherein said definitions aryl and acylamino have meaning as defined in said claim; or a pharmaceutically acceptable salt thereof.

3. A compound having the formula

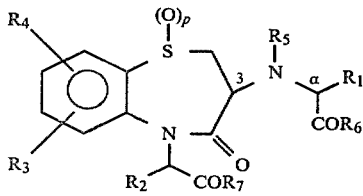

(II)

wherein $R_1$ is hydrogen, lower alkyl, amino-lower alkyl, acylamino-lower alkyl, aryl, aryl-lower alkyl, or cycloalkyl-lower alkyl;

$R_2$ and $R_5$ represent hydrogen or lower alkyl;

$R_3$ and $R_4$ represent hydrogen, lower alkyl, lower alkoxy, lower alkanoyloxy, hydroxy, halogen or trifluoromethyl; or $R_3$ and $R_4$ taken together represent lower alkylenedioxy;

p represents zero, one or two;

$R_6$ and $R_7$ independently represent hydroxy, amino, mono- or di-lower alkylamino, lower alkoxy, aryl-lower alkoxy, lower alkanoyloxymethoxy, (amino, mono- or di-lower alkylamino, carboxy, lower alkoxycarbonyl or bicyclo [2,2,1]-heptyloxycarbonyl)-lower alkoxy; and wherein within the above definitions acylamino represents lower alkanoylamino; lower alkoxycarbonylamino; aryl(lower)alkanoylamino; aryl(lower)alkoxycarbonylamino; or aroylamino in which aroyl represents benzoyl or benzoyl substituted by lower alkyl, lower alkoxy or halogen, or nicotinoyl; and wherein within the above definitions aryl represents phenyl unsubstituted or mono- or di-substituted by lower alkyl, lower alkoxy, lower alkylenedioxy, lower alkanoyloxy, hydroxy, halogen or trifluoromethyl; and cycloalkyl contains 3 to 8 carbons; or a pharmaceutically acceptable salt thereof.

4. A compound of claim 3 wherein $R_1$ is hydrogen, lower alkyl, amino-lower alkyl, acylamino-lower alkyl, aryl-lower alkyl where aryl represents phenyl unsubstituted or mono- or disubstituted by lower alkyl, hydroxy, lower alkoxy, lower alkylenedioxy, lower alkanoyloxy, halogen or trifluoromethyl;

$R_2$ and $R_5$ are hydrogen or lower alkyl;

$R_3$ and $R_4$ are hydrogen, lower alkoxy, lower alkyl, halogen or trifluoromethyl; or $R_3$ and $R_4$ taken together represent alkylenedioxy;

p represents zero, one or two;

$R_6$ and $R_7$ independently represent hydroxy, amino, lower alkoxy, phenyl-lower alkoxy, pyridyl-lower alkoxy, lower alkanoyloxymethoxy, lower alkoxycarbonyl-lower alkoxy, or bicyclo[2,2,1]heptyloxycarbonylmethoxy;

a pharmaceutically acceptable salt thereof.

5. A compound of claim 3 having the formula

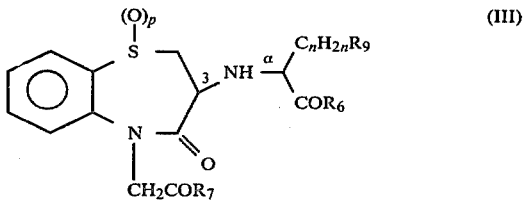

(III)

wherein n represents an integer from 1 to 4; p is zero, one or two;

$R_9$ is hydrogen, amino, benzyloxycarbonylamino, phenyl unsubstituted or monosubstituted by lower alkyl, lower alkoxy, lower alkanoyloxy, halogen, hydroxy, or trifluoromethyl;

$R_6$ and $R_7$ independently represent hydroxy, lower alkoxy of up to 4 carbon atoms, benzyloxy, amino;

or a pharmaceutically acceptable salt thereof.

6. A compound of claim 5 and formula III wherein $C_nH_{2n}$ represents ethylene; $R_9$ represents phenyl or phenyl monosubstituted by lower alkoxy with up to 4 carbon atoms, lower alkyl with up to 4 carbon atoms, halogen or trifluoromethyl; p is zero or one;

$R_6$ and $R_7$ independently represent hydroxy or lower alkoxy with up to 4 carbon atoms;

or a pharmaceutically acceptable salt thereof.

7. A compound of claim 1 having the formula

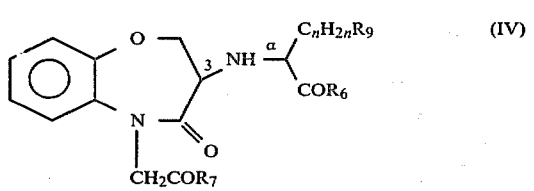

(IV)

n represents an integer from 1 to 4;

$R_9$ is hydrogen, amino, benzyloxycarbonylamino, phenyl unsubstituted or monosubstituted by lower alkyl, lower alkoxy, lower alkanoyloxy, halogen, hydroxy, or trifluoromethyl;

$R_6$ and $R_7$ independently represent hydroxy or lower alkoxy of up to 4 carbon atoms; or a pharmaceutically acceptable salt thereof.

8. A compound of claim 7 and formula IV wherein $C_nH_{2n}$ represents ethylene; $R_9$ represents phenyl or phenyl mono-substituted by lower alkoxy with up to 4 carbon atoms, lower alkyl with up to 4 carbon atoms, halogen or trifluoromethyl;

$R_6$ and $R_7$ independently represent hydroxy or lower alkoxy with up to 4 carbon atoms;

or a pharmaceutically acceptable salt thereof.

9. A compound of claim 3 wherein the ring carbon atom 3 is of the R-configuration and the side chain carbon atom is of the S-configuration; or a pharmaceutically acceptable salt thereof.

10. A compound of claim 7 wherein both the ring carbon atom 3 and the side chain carbon atom are of S-configuration.

11. A compound as claimed in claim 5 being 3-[N-(1-carboethoxy-3-phenylpropyl)amino]-5-carboxymethyl-2,3-dihydro-1,5-benzothiazepin-4(5H)-one, a stereoisomer or a pharmaceutically acceptable salt thereof.

12. A compound as claimed in claim 5 being 3-[N-(1-carboxy-3-phenylpropyl)amino]-5-carboxymethyl-2,3-dihydro-1,5-benzothiazepin-4(5H)-one, a stereoisomer or a pharmaceutically acceptable salt thereof.

13. A compound as claimed in claim 5 being 3-[N-(1-carboxy-3-phenylpropyl)amino]-5-carboxymethyl-2,3-dihydro-1-oxo-1,5-benzothiazepin-4(5H)-one, a stereoisomer or a pharmaceutically acceptable salt thereof.

14. A compound as claimed in claim 7 being 3-[N-(1-carboxy-3-phenylpropyl)amino]-5-carboxymethyl-2,3-dihydro-1,5-benzoxa-zepin-4(5H)-one, a stereoisomer or a pharmaceutically acceptable salt thereof.

15. A compound as claimed in claim 5 being 3-[N-(1-carboxy-5-aminopentyl)amino]-5-carboxymethyl-2,3-dihydro-1,5-benzothiazepin-4(5H)-one, a stereoisomer or a pharmaceutically acceptable salt thereof.

16. A pharmaceutical composition suitable for oral or parenteral administration to mammals for the treatment or prevention of diseases responsive to inhibition of angiotensin-converting enzyme comprising an effective amount of a compound of claim 1 in combination with one or more pharmaceutically acceptable carriers.

17. A method of treating hypertensive or cardiac conditions in mammals which comprises administering to a mammal in need thereof an effective amount of a composition of claim 16.

18. A method of inhibiting angiotensin-converting enzyme which comprises administering to a mammal in need thereof an effective amount of a composition of claim 16.

* * * * *